(12) United States Patent
Reed et al.

(10) Patent No.: US 7,438,203 B2
(45) Date of Patent: *Oct. 21, 2008

(54) DERMAL PENETRATION ENHANCERS AND DRUG DELIVERY SYSTEMS INVOLVING SAME

(75) Inventors: Barry Lenard Reed, Strathmore (AU); Timothy Matthias Morgan, Carlton North (AU); Barrie Charles Finnin, Glen Iris (AU)

(73) Assignee: Acrux DDS Pty Ltd, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 10/759,303

(22) Filed: Jan. 20, 2004

(65) Prior Publication Data
US 2004/0146469 A1 Jul. 29, 2004

Related U.S. Application Data

(60) Continuation of application No. 09/910,780, filed on Jul. 24, 2001, now Pat. No. 6,818,226, which is a division of application No. 09/125,436, filed as application No. PCT/AU97/00091 on Feb. 19, 1997, now Pat. No. 6,299,900.

(30) Foreign Application Priority Data
Feb. 19, 1996 (AU) .................. PN8144/96

(51) Int. Cl.
*G01F 11/00* (2006.01)
*A61F 13/02* (2006.01)
*A61K 9/70* (2006.01)

(52) U.S. Cl. .................. 222/282; 424/448; 424/449

(58) Field of Classification Search .................. 424/400, 424/59, 448, 449; 222/282
See application file for complete search history.

(56) References Cited

U.S. PATENT DOCUMENTS

| 3,306,252 | A | * | 2/1967 | Knight et al. ................ 118/710 |
| 3,989,816 | A |   | 11/1976 | Rajadhyaksha |
| 4,299,826 | A |   | 11/1981 | Luedders |
| 4,310,511 | A |   | 1/1982 | Holick |
| 4,440,777 | A |   | 4/1984 | Zupan |

(Continued)

FOREIGN PATENT DOCUMENTS

AU 30258/89 9/1989

(Continued)

OTHER PUBLICATIONS

R. J. Feldmann et al., "Percutaneous Penetration of 14C Hydrocortisone In Man", *Arch Derm*, vol. 94:649-651, (1966).

(Continued)

*Primary Examiner*—Johann Richter
*Assistant Examiner*—Konata M George
(74) *Attorney, Agent, or Firm*—Foley & Lardner

(57) ABSTRACT

The invention relates to a method for treatment or prophylaxis of a disease or condition in an animal comprising administering to a mucosal membrane of said animal in need of such treatment a therapeutically effective amount of a drug delivery system comprising at least one physiologically active agent or prodrug thereof and at least one penetration enhancer selected from safe ester sunscreens.

5 Claims, 9 Drawing Sheets

U.S. PATENT DOCUMENTS

| | | | |
|---|---|---|---|
| 4,557,934 A | 12/1985 | Cooper | |
| 4,563,346 A | 1/1986 | Deckner | |
| 4,663,157 A | 5/1987 | Brock | |
| 4,699,779 A | 10/1987 | Palinczar | |
| 4,704,406 A | 11/1987 | Stanislaus et al. | 514/570 |
| 4,820,724 A | 4/1989 | Nimni | |
| 4,938,951 A | 7/1990 | Leung et al. | |
| 4,946,671 A | 8/1990 | Bissett et al. | |
| 4,954,487 A | 9/1990 | Cooper et al. | |
| 4,959,205 A | 9/1990 | Brunner et al. | |
| 4,975,272 A | 12/1990 | Voyt | |
| 5,030,442 A | 7/1991 | Uster et al. | |
| 5,034,386 A | 7/1991 | Peck et al. | 514/212 |
| 5,036,100 A | 7/1991 | Deboeck et al. | |
| 5,082,866 A | 1/1992 | Wong et al. | 514/785 |
| 5,100,918 A * | 3/1992 | Sunshine et al. | 514/557 |
| 5,122,519 A | 6/1992 | Ritter | |
| 5,192,534 A | 3/1993 | Grollier et al. | |
| 5,256,647 A | 10/1993 | Minaskanian et al. | 514/24 |
| 5,413,794 A | 5/1995 | Suzuki et al. | |
| 5,426,210 A | 6/1995 | Kato et al. | |
| 5,446,025 A | 8/1995 | Lu et al. | |
| 5,449,519 A | 9/1995 | Wolf et al. | |
| 5,487,898 A | 1/1996 | Lu et al. | |
| 5,573,754 A | 11/1996 | Kulkarni et al. | |
| 5,674,912 A | 10/1997 | Martin | |
| 5,679,374 A | 10/1997 | Fanchon et al. | |
| 5,804,168 A | 9/1998 | Murad | 424/439 |
| 5,951,967 A | 9/1999 | Golz et al. | |
| 6,004,969 A | 12/1999 | Hu | |
| 6,010,716 A | 1/2000 | Saunal et al. | |
| 6,211,250 B1 | 4/2001 | Tomlinson et al. | |
| 6,299,900 B1 * | 10/2001 | Reed et al. | 424/449 |
| 6,818,226 B2 * | 11/2004 | Reed et al. | 424/449 |
| 6,916,486 B2 * | 7/2005 | Klose et al. | 424/448 |
| 6,916,487 B2 * | 7/2005 | Klose et al. | 424/448 |
| 6,923,983 B2 * | 8/2005 | Morgan et al. | 424/448 |
| 6,929,801 B2 * | 8/2005 | Klose et al. | 424/448 |
| 2004/0096405 A1 * | 5/2004 | Chew et al. | 424/59 |
| 2005/0186141 A1 | 8/2005 | Gonda et al. | |

FOREIGN PATENT DOCUMENTS

| | | |
|---|---|---|
| AU | 49984/1990 | 9/1989 |
| AU | A-30258/89 | 9/1989 |
| AU | A-49984/90 | 9/1990 |
| AU | 91413/91 | 6/1992 |
| CA | 2 218 534 | 6/1996 |
| DE | 43 34 553 | 4/1995 |
| EP | 0 189 861 | 8/1986 |
| EP | 189 861 | 8/1986 |
| EP | 0 332 147 | 9/1989 |
| EP | 0 552 405 | 7/1993 |
| EP | 0 552 405 A1 | 7/1993 |
| EP | 0 581 587 A2 | 2/1994 |
| EP | 0 614 354 B1 | 9/1994 |
| EP | 0608 322 B1 | 7/1998 |
| JP | 61-268631 | 11/1986 |
| WO | WO 92/10154 | 6/1992 |
| WO | 92/19271 | 11/1992 |
| WO | WO 92/20376 A1 | 11/1992 |
| WO | WO 93/10755 A1 | 6/1993 |
| WO | WO 96/17624 | 6/1996 |
| WO | 96/30000 | 10/1996 |
| WO | WO 96/41613 | 12/1996 |

OTHER PUBLICATIONS

M. F. Coldman et al., "Enhancement Of Percutaneous Absorption by The Use Of Volatile: Nonvolatile Systems And Vehicles", *Journal of Pharmaceutical Sciences*, vol. 58(9):1098-1102, (1969).

P. P. Bhatt, et al., "Finite Dose Transport Of Drugs In Liquid Formulations Through Stratum Corneum: Analytical Solution To A Diffusion Model", *International Journal Of Pharmaceutics*, Elsevier science Publishers B. V., vol. 50:197-203, (1989).

Nimni, U.S. Patent No. 4,820,742, Internet: www.patents.ibm.com/fegi-bin/any2htm Document "Dual phase Solvent Carrier System", pp. 3, 4 and 6 out of 7 pages.

Bucks et al., Percutaneous Absorption of Hydroquinone in Humans: Effect of 1-Dodecylazacycloheptan-2-One (Azone) and the 2-Ethylhexyl Ester of 4-(Dimethylamino) Benzoic Acid (Escalol 507), Journal of Toxicology and Environmental Health, 24:279-289 (1988).

Physicians' Desk Reference (49 Ed.) 1995, .pp. 1151-1152, Medical Economics Company, Inc., Montvale, N.J.

Good et al., "A New Transdermal Delivery System for Estraiol," Journal of Controlled Release 2:89-97 (1985) © Elsevier Science Publishers B.V., Amsterdam—Printed in The Netherlands.

Apr. 3, 2007 Office Action from related U.S. Appl. No. 11/513,342 (8 pgs.).

Office Action issued Jul. 11, 2007 in U.S. Appl. No. 11/517,575 (7 pgs.).

* cited by examiner

DERMAL PENETRATION ENHANCERS AND DRUG DELIVERY SYSTEMS INVOLVING SAME

This application is a continuation of U.S. patent application Ser. No. 09/910,780 filed on Jul. 24, 2001, now U.S. Pat. No. 6,818,226, which is a divisional of Ser. No. 09/125,436 U.S. Pat. No. 6,299,900, filed Dec. 18, 1998 as the U.S. national stage application of PCT application PCT/AU97/00091, filed Feb. 19, 1997, The entire contents of each of U.S. patent application Ser. No. 09/910,780, U.S. Pat. No. 6,299,900, and PCT application PCT/AU97/00091 are incorporated herein by reference, and priority to each is claimed under 35 U.S.C § 119 and/or § 120.

FIELD OF THE INVENTION

The present invention relates to percutaneous or transdermal drug delivery. More specifically, the invention relates to a topical absorption/penetration enhancing agent for use in the delivery of a physiologically active agent to an animal, including a human. The invention also relates to a system for the non-occlusive delivery to an animal of a physiologically active agent across a dermal surface or mucosal membrane of the animal. Transdermal drug formulations of the present invention may be used for local application or systemic delivery.

BACKGROUND OF THE INVENTION

The prevention or treatment of local or topical disease states or conditions of the skin has traditionally used simple non-occlusive delivery systems. These drug delivery systems usually include a volatile and/or non-volatile medium whereby a composition of the drug and medium is topically applied to the skin, generally in the vicinity of or directly on the area of skin to be treated. Such delivery systems usually take the form of emulsions, creams, ointments, foams, gels, liquids, sprays and aerosols. These delivery systems are generally used to treat skin inflammations, soft-tissue contusions, parasites, fungal and bacterial topical infection and topical analgesia. The limitation with this type of delivery system is that systemic drugs are generally not suitable for this type of administration. Some major problems with the current state of the art relate to a lack of efficacy of systemic drugs because of the low drug flux across the skin, as observed for drugs such as testosterone, amlodipine, fentanyl, buprenorphine and many others. Other drugs, such as glyceryl trinitrate, Nitrobid™ (a drug for the treatment of angina), are difficult to deliver by these systems due to the inability to adequately control the rate of drug delivery, or the requirement for a very large application area. Other problems with the poor dermal penetration of drugs is that the drug can be easily washed off or transferred to clothes, other surfaces or other animals.

The dermal delivery of drugs may represent the oldest form of drug delivery in human history. Resins and animal fats were probably used by humans in early times to treat damage to the skin resulting from injuries and burns. Such substances for local delivery of active substances remained largely unchanged until as late as this century. The concept of transdermal systemic drug delivery was first seriously advocated by Dr Alejandro Zaffaroni in U.S. Pat. Nos. 3,598,122, 3,731,683 and 3,797,494 from the early 1970s. Transdermal systemic drug delivery provides an effective method of achieving improved bioavailability for physiologically active substances where the drugs are poorly absorbed by traditional routes of delivery. It can also be used where oral dosing is poorly tolerated or not possible.

Transdermal formulations are however limited. For example polar drugs tend to penetrate the skin too slowly. Since most drugs are of a polar nature this limitation is significant, as is the fact that many drugs cause irritation at the site of topical application.

Two main methods are known for assisting the rate of penetration of drugs across the skin. The first is to increase the thermodynamic activity of the drug. The thermodynamic activity of a drug in a dermal formulation is proportional to the concentration of the drug and the selection of the vehicle. According to the laws of thermodynamics, the maximum activity of a drug is related to that of the pure drug crystal. The second method involves the use of compounds known as penetration enhancers to increase the permeability of the dermal surface and has generally proven to be more convenient and effective.

Since the early 1970s the main focus of transdermal systemic drug delivery has been, and still is, on transdermal patch devices. These patch devices are like bandages which are attached to the surface of intact skin for prolonged periods of time to allow a desired systemic delivery of a drug or other physiologically active agent. These transdermal patch devices occlude the skin and trap the drug, together with volatiles and vehicle excipients, between the skin and an outer impermeable backing membrane. The membrane prevents the evaporation or diffusion of vehicle excipients, volatiles and drug into an environment other than the target skin site. The prolonged length of time required for transfer of the drug and excipients from the patch into the skin can and often does result in local skin irritation. The irritation is caused by prolonged contact on the skin by the drug, volatiles, vehicle excipients, or the adhesive used to attach the patch device to the skin. The occlusive nature of the patch device also restricts the natural ability of the skin to "breathe", increasing the risk of irritation. With added problems of complex and costly manufacturing processes for transdermal patch devices there is a need for improved transdermal drug delivery systems.

The rate of drug delivery across a dermal surface can be increased by dermal penetration enhancers. The problem with most known dermal penetration enhancers is that they are often toxic, irritating or allergenic. These enhancers tend to be proton accepting solvents such as dimethylsulfoxide and dimethyacetamide. More recently, 2-pyrrolidine, N,N-diethyl-m-toluamide (Deet), 1-dodecal-azacycloheptane-2-one (Azone®), N,N-dimethylformamide, N-methyl-2-pyrrolidine and calcium thioglycolate have been reported as effective enhancers. However, difficulties remain with such dermal enhancers because the problem of irritation at the site of application has not been overcome.

The most critical problem with these compounds however is their toxicity. If a compound when used as a dermal enhancer is toxic, irritating or allergenic, then that compound is unsuitable for application to the animal body. Dimethyl sulfoxide and dimethyl acetamide are not clinically acceptable for these reasons. Although Deet and Azone® have lower reported toxicities, their toxicity is still such that they are not widely used. It is possible that Azone® may be employed as a dermal penetration enhancer if the amount applied is sufficiently small so as not to be appreciably toxic, irritating or allergenic to the animal.

The thermodynamic activity of a drug can be increased by employing supersaturated systems which give rise to unusually high thermodynamic potentials [Coldman, et al., J. Pharm. Sci., 58(9), 119, 1969]. However, topical vehicles relying on supersaturation, have the major limitation of formulation instability, both prior to and during application to the skin. As such, they are of limited clinical value within a non-occlusive volatile:non-volatile delivery vehicle, because as soon as the formulation comes into contact with a person's clothing or the like, the drug often precipitates; hence the formulation is no longer supersaturated and any enhanced percutaneous absorption ceases.

Other workers such as Kondo, et al., [J. Pharmacobio-Dyn., 10, 743, 1987] who were using supersaturation to achieve enhanced transdermal drug delivery, have relied on the use of anti-nucleating polymers to stabilize the formulation. However, the applied drug formulations stabilised with polymers formed an appreciable surface mass on the skin which remained there over a prolonged duration of many hours, not a few minutes. So while Kondo advocated the use of a metered spray to deliver these formulations, in reality it would be impossible to obtain a non-occlusive delivery system with a short application time and still maintain a clinically useful transdermal penetration enhancement.

German patent application DE 4334553-A1 to Jenapharm GmbH discloses a pharmaceutical liquid system consisting of a drug (diclofenac), a lipophilic phase, a volatile component and appropriate antioxidants, preservatives or stabilisers. This system relies on supersaturation to increase the flux rate of dermal absorption. An application chamber is used to prevent accidental precipitation of the supersaturated drug delivery system over the application time of 150 minutes.

Japanese patent JP 61-268631 to Showa Denko KK discloses dermal penetration enhancers suitable for use with water-soluble drugs. The dermal penetration enhancers disclosed include 1-5 carbon fatty acid esters of para-aminobenzoic acid but their chemical structures are quite distinct from the compounds used in the present invention, and the physicochemical properties of the 1-5 carbon fatty acid esters of para-aminobenzoic acid are markedly different to those of the present invention. For example the octanol-water partition coefficients for all the 1-5 carbon fatty acid esters of para-aminobenzoic acid are at least 200 fold lower than those of the present invention. Also the preferred dermal penetration enhancer disclosed in JP 61-268631 is the 2 carbon fatty acid ester of para-aminobenzoic acid (or Benzocaine) which has an octanol-water partition coefficient which is more than 8000 fold lower than those of the present invention. Unlike those of the present invention, the preferred dermal penetration enhancer disclosed in JP 61-268631 has significant pharmacological properties in that it is a local anaesthetic, which has also been reported to cause irritant and allergic skin reactions. The compounds used in the present invention fulfil the ideal properties of a dermal penetration enhancer in that they are non-irritant and pharmacologically inert [Barry, B. W. Vehicle Effect: What Is an Enhancer? In: Topical Drug Bioavailability, Bioequivalence, and Penetration. Shah, V. P.; Maibach, H. I. Eds. Plenum Press: New York, 1993; pp 261-276.].

It was not surprising then to find that in previous studies [Feldmann, et al., Arch. Derm., 94, 649, 1996; Coldman, et al., J. Pharm. Sci., 58(9), 119, 1969; and Bhatt, et al., Int. J. Pharm., 50, 157, 1989] where low volumes of non-occlusive volatile:non-volatile vehicles had been applied to the skin, the extent of drug delivery was very limited. To date the only formulations that have been employed clinically are either for local therapies, such as topical minoxidil and topical non-steroidal anti-inflammatories, or for transdermal drug delivery of compounds which readily diffuse across the skin such as glyceryl trinitrate and isosorbide dinitrate. As the permeability coefficients of sex hormones, for example, are an order of magnitude lower than glyceryl trinitrate, a marked penetration enhancement effect would be needed to achieve clinically acceptable transdermal drug delivery.

It is desirable to have a clinically acceptable non-occlusive transdermal drug delivery system where the drug and penetration enhancer undergoes rapid partitioning into the skin to allow a convenient application time, leaving no residual formulation on the skin surface, and maintaining good substantivity within the skin. These characteristics can overcome problems such as a loss of drug penetration or possibly a transfer of the drug from the treated individual to another upon intimate contact, such as that observed for a testosterone ointment being used for a male patient, but which caused virilization in his female sexual partner [Delance, et al., Lancet, 1, 276,–1984].

It is an object of the present invention to overcome or at least alleviate one or more of the abovementioned disadvantages of the prior art systems.

SUMMARY OF THE INVENTION

According to a first aspect of the present invention there is provided a transdermal drug delivery system which comprises at least one physiologically active agent or prodrug thereof and at least one dermal penetration enhancer; characterised in that the dermal penetration enhancer is a safe skin-tolerant ester sunscreen.

The present invention also provides use of a safe skin-tolerant ester sunscreen as a dermal penetration enhancer.

The present inventors have found a new class of dermal penetration enhancers being skin-tolerant ester sunscreens, which are generally considered safe by the FDA (U.S.). Compounds such as octyl dimethyl-para-aminobenzoate (Padimate O) and octyl salicylate have been extensively used over the last ten to twenty years as safe and effective sunscreens in concentrations up to 8% v/v for Padimate O and 5% v/v for octyl salicylate.

Dermal penetration enhancers of the present invention are preferably esters of formula (I):

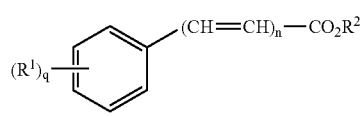

wherein R.sup.1 is hydrogen, lower alkyl, lower alkoxy, halide, hydroxy or $NR^3R^4$;
$R^2$ is long chain alkyl;
$R^3$ and $R^4$ are each independently hydrogen, lower alkyl or $R^3$ and $R^4$ together with the nitrogen atom to which they are attached form a 5- or 6-membered heterocyclic ring;
n is 0 or 1; and
q is 1 or 2.

More preferably the ester is a long chain alkyl para-aminobenzoate, long chain alkyl dimethyl-para-aminobenzoate, long chain alkyl cinnamate, long chain alkyl methoxycinnamate or long chain alkyl salicylate; most preferably octyl dimethyl-para-aminobenzoate, octyl para-methoxycinnamate, octyl salicylate or isoamyl salicylate.

DETAILED DESCRIPTION OF THE INVENTION

The drug delivery systems according to the invention may comprise any physiologically active agent together with the penetration enhancer incorporated into a dosage form for topical application to the skin or mucous membranes of animals. Suitable dosage forms include creams, lotions, gels, ointments, suppositories, mousses, spray, for example nasal sprays, aerosols, buccal and sublingual tablets, gingival and buccal patches or any one of a variety of transdermal devices for use in the continuous administration of systematically active drugs by absorption through the skin, oral mucosa or other membranes. Some examples of suitable vehicles are given in U.S. Pat. Nos. 3,598,122, 3,598,123, 3,742,951, 3,814,097, 3,921,636, 3,993,072, 3,993,073, 3,996,934, 4,031,894, 4,060,084, 4,069,307, 4,201,211, 4,230,105, 4,292,299, 4,292,303, 5,323,769, 5,023,085, 5,474,783, 4,941,880 and U.S. Pat. No. 4,077,407. These patents also disclose a variety of specific systematically active agents which may also be useful in transdermal delivery in adjunct to those of this invention. These disclosures are thus hereby incorporated herein by reference.

Physiologically active agents that may be used in the percutaneous or transdermal drug delivery system of the present invention include any locally or systemically active agents which are compatible with the dermal penetration enhancers of the present invention and which can be delivered through the skin with the assistance of the dermal penetration enhancer to achieve a desired effect. These active agents (grouped by therapeutic class) include:

Alimentary System

Antidiarrhoeals such as diphenoxylate, loperamide and hyoscyamine.

Cardiovascular System

Antihypertensives such as hydralazine, minoxidil, captopril, enalapril, clonidine, prazosin, debrisoquine, diazoxide, guanethidne, methyldopa, reserpine, trimetaphan. Calcium channel blockers such as diltiazem, felodopine, amlodipine, nitrendipine, nifedipine and verapamil.

Antiarrhyrthmics such as amiodarone, flecainide, disopyramide, procainamide, mexiletene and quinidine.

Antiangina agents such as glyceryl trinitrate, erythritol tetranitrate, pentaerythritol tetranitrate, mannitol hexanitrate, perhexilene, isosorbide dinitrate and nicorandil.

Beta-adrenergic blocking agents such as alprenolol, atenolol, bupranolol, carteolol, labetalol, metoprolol, nadolol, nadoxolol, oxprenolol, pindolol, propranolol, sotalol, timolol and timolol maleate.

Cardiotonic glycosides such as digoxin and other cardiac glycosides and theophylline derivatives.

Adrenergic stimulants such as adrenaline, ephedrine, fenoterol, isoprenaline, orciprenaline, rimeterol, salbutamol, salmeterol, terbutaline, dobutamine, phenylephrine, phenylpropanolamine, pseudoephedrine and dopamine. Vasodilators such as cyclandelate, isoxsuprine, papaverine, dipyrimadole, isosorbide dinitrate, phentolamine, nicotinyl alcohol, co-dergocrine, nicotinic acid, glyceryl trinitrate, pentaerythritol tetranitrate and xanthinol.

Antimigraine preparations such as ergotamine, dihydroergotamine, methysergide, pizotifen and sumatriptan.

Drugs Affecting Blood and Haemopoietic Tissues.

Anticoagulants and thrombolytic agents such as warfarin, dicoumarol, low molecular weight heparins such as enoxaparin; streptokinase and its active derivatives. Haemostatic agents such as aprotinin, tranexamic acid and protamine.

Central Nervous System

Analgesics, antipyretics including the opiod analgesics- such as buprenorphine, dextromoramide, dextropropoxyphene, fentanyl, alfentanil, sufentanil, hydromorphone, methadone, morphine, oxycodone, papaveretum, pentazocine, pethidine, phenoperidine, codeine and dihydrocodeine. Others include acetylsalicylic acid (aspirin), paracetamol, and phenazone.

Hypnotics and sedatives such as the barbiturates, amylobarbitone, butobarbitone and pentobarbitone and other hypnotics and sedatives such as choral hydrate, chlormethiazole, hydroxyzine and meprobamate.

Antianxiety agents such as the benzodiazepines, alprazolam, bromazepam, chlordiazepoxide, clobazam, chlorazepate, diazepam, flunitrazepam, flurazepam, lorazepam, nitrazepam, oxazepam, temazepam and triazolam. Neuroleptic and antipsychotic drugs such as the phenothiazines, chlorpromazine, fluphenazine, pericyazine, perphenazine, promazine, thiopropazate, thioridazine and trifluoperazine and the butyrophenones, droperidol and haloperidol and the other antipsychotic drugs such as pimozide, thiothixene and lithium.

Antidepressants such as the tricyclic antidepressants amitryptyline, clomipramine, desipramine, dothiepin, doxepin, imipramine, nortriptyline, opipramol, protriptyline and trimipramine and the tetracyclic antidepressants such as mianserin and the monoamine oxidase inhibitors such as isocarboxazid, phenelizine, tranylcypromine and moclobemide and selective serotonin re-uptake inhibitors such as fluoxetine, paroxetine, citalopram, fluvoxamine and sertraline.

CNS Stimulants Such as Caffeine

Anti-Alzheimer's Agents Such as Tacrine

Antiparkinson agents such as amantadine, benserazide, carbidopa, levodopa, benztropine, biperiden, benzhexol, procyclidine and dopamine-2 agonists such as S(−)-2-(N-propyl-N-2-thienylethylamino)-5-hydroxytetrali-n (N-0923).

Anticonvulsants such as phenytoin, valproic acid, primidone, phenobarbitone, methylphenobarbitone and carbamazepine, ethosuximide, methsuximide, phensuximide, sulthiame and clonazepam.

Antiemetics, antinauseants such as the phenothiazines, prochloperazine, thiethylperazine and 5HT-3 receptor antagonists such as ondansetron and granisetron and others such as dimenhydrinate, diphenhydramine, metoclopramide, domperidone, hyoscine, hyoscine hydrobromide, hyoscine hydrochloride, clebopride and brompride.

Musculoskeletal System

Non-steroidal anti-inflammatory agents including their racemic mixtures or individual enantiomers where applicable, such as ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol and ketoralac.

Additional non-steroidal antiinflammatory agents which can be formulated in combination with the dermal penetration enhancers include salicylamide, salicylic acid, flufenisal, salsalate, triethanolamine salicylate, aminopyrine, antipyrine, oxyphenbutazone, apazone, cintazone, flufenamic acid, clonixeril, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloide, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate.

Antirheumatoid agents such as penicillamine, aurothioglucose, sodium aurothiomalate, methotrexate and auranofin.

Muscle relaxants such as baclofen, diazepam, cyclobenzaprine hydrochloride, dantrolene, methocarbamol, orphenadrine and quinine.

Agents used in gout and hyperuricaemia such as allopurinol, colchicine, probenecid and sulphinpyrazone.

Hormones and Steroids

Oestrogens such as oestradiol, oestriol, oestrone, ethinyloestradiol, mestranol, stilboestrol, dienoestrol, epioestriol, estropipate and zeranol. Progesterone and other progestagens such as allyloestrenol, dydrgesterone, lynoestrenol, norgestrel, norethyndrel, norethisterone, norethisterone acetate, gestodene, levonorgestrel, medroxyprogesterone and megestrol.

Antiandrogens such as cyproterone acetate and danazol.

Antioestrogens such as tamoxifen and epitiostanol and the aromatase inhibitors, exemestane and 4-hydroxy-androstenedione and its derivatives. Androgens and anabolic agents such as testosterone, methyltestosterone, clostebol acetate, drostanolone, furazabol, nandrolone oxandrolone, stanozolol, trenbolone acetate, dihydro-testosterone, 17-α-methyl-19-nortestosterone and fluoxymesterone. 5-alpha reductase inhibitors such as finasteride, turosteride, LY-191704 and MK-306.

Corticosteroids such as betamethasone, betamethasone valerate, cortisone, dexamethasone, dexamethasone 21-phosphate, fludrocortisone, flumethasone, fluocinonide, fluocinonide desonide, fluocinolone, fluocinolone acetonide, fluocortolone, halcinonide, halopredone, hydrocortisone, hydrocortisone 17-valerate, hydrocortisone 17-butyrate, hydrocortisone 21-acetate methylprednisolone, prednisolone, prednisolone 21-phosphate, prednisone, triamcinolone, triamcinolone acetonide.

Further examples of steroidal antiinflammatory agents for use in the instant compositions include include cortodoxone, fluoracetonide, fludrocortisone, difluorsone diacetate, flurandrenolone acetonide, medrysone, amcinafel, amcinafide, betamethasone and its other esters, chloroprednisone, clorcortelone, descinolone, desonide, dichlorisone, difluprednate, flucloronide, flumethasone, flunisolide, flucortolone, fluoromethalone, fluperolone, fluprednisolone, meprednisone, methylmeprednisolone, paramethasone, cortisone acetate, hydrocortisone cyclopentylpropionate, cortodoxone, flucetonide, fludrocortisone acetate, flurandrenolone acetonide, medrysone, amcinafal, amcinafide, betamethasone, betamethasone benzoate, chloroprednisone acetate, clocortolone acetate, descinolone acetonide, desoximetasone, dichlorisone acetate, difluprednate, flucloronide, flumethasone pivalate, flunisolide acetate, fluperolone acetate, fluprednisolone valerate, paramethasone acetate, prednisolamate, prednival, triamcinolone hexacetonide, cortivazol, formocortal and nivazol.

Pituitary hormones and their active derivatives or analogs such as corticotrophin, thyrotropin, follicle stimulating hormone (FSH), luteinising hormone (LH) and gonadotrophin releasing hormone (GnRH).

Hypoglycaemic agents such as insulin, chlorpropamide, glibenclamide, gliclazide, glipizide, tolazamide, tolbutamide and metformin.

Thyroid hormones such as calcitonin, thyroxine and liothyronine and antithyroid agents such as carbimazole and propylthiouracil.

Other miscelaneous hormone agents such as octreotide.

Pituitary inhibitors such as bromocriptine.

Ovulation inducers such as clomiphene.

Genitourinary System

Diuretics such as the thiazides, related diuretics and loop diuretics, bendrofluazide, chlorothiazide, chlorthalidone, dopamine, cyclopenthiazide, hydrochlorothiazide, indapamide, mefruside, methycholthiazide, metolazone, quinethazone, bumetamide, ethacrynic acid and frusemide and pottasium sparing diuretics, spironolactone, amiloride and triamterene.

Antidiuretics such as desmopressin, lypressin and vasopressin including their active derivatives or analogs.

Obstetric drugs including agents acting on the uterus such as ergometrine, oxytocin and gemeprost.

Prostaglandins such as alprostadil (PGE1), prostacyclin (PGI2), dinoprost (prostaglandin F2-alpha) and misoprostol.

Antimicrobials

Antimicrobials including the cephalosporins such as cephalexin, cefoxytin and cephalothin.

Penicillins such as amoxycillin, amoxycillin with clavulanic acid, ampicillin, bacampicillin, benzathine penicillin, benzylpenicillin, carbenicillin, cloxacillin, methicillin, phenethicillin, phenoxymethylpenicillin, flucloxacillin, meziocillin, piperacillin, ticarcillin and aziocillin.

Tetracyclines such as minocycline, chlortetracycline, tetracycline, demeclocycline, doxycycline, methacycline and oxytetracycline and other tetracycline-type antibiotics.

Aminoglycosides such as amikacin, gentamicin, kanamycin, neomycin, netilmicin and tobramycin.

Antifungais such as amorolfine, isoconazole, clotrimazole, econazole, miconazole, nystatin, terbinafine, bifonazole, amphotericin, griseofulvin, ketoconazole, fluconazole and flucytosine, salicylic acid, fezatione, ticlatone, tolnaftate, triacetin, zinc, pyrithione and sodium pyrithione.

Quinolones such as nalidixic acid, cinoxacin, ciprofloxacin, enoxacin and norfloxacin. Sulphonamides such as phthalylsulphthiazole, sulfadoxine, sulphadiazine, sulphamethizole and sulphamethoxazole.

Sulphones such as dapsone.

Other miscellaneous antibiotics such as chloramphenicol, clindamycin, erythromycin, erythromycin ethyl carbonate, erythromycin estolate, erythromycin glucepate, erythromycin ethylsuccinate, erythromycin lactobionate, roxithromycin, lincomycin, natamycin, nitrofurantoin, spectinomycin, vancomycin, aztreonam, colistin IV, metronidazole, timidazole, fusidic acid and trimethoprim; 2-thiopyridine N-oxide; halogen compounds, particularly iodine and iodine compounds such as iodine-PVP complex and diiodohydroxyquin; hexachlorophene; chlorhexidine; chloroamine compounds; benzoylperoxide.

Antituberculosis drugs such as ethambutol, isoniazid, pyrazinamide, rifampicin and clofazimine.

Antimalarials such as primaquine, pyrimethamine, chloroquine, hydroxychloroquine, quinine, mefloquine and halofantrine.

Antiviral agents such as acyclovir and acyclovir prodrugs, famciclovir, zidovudine, didanosine, stavudine, lamivudine, zalcitabine, saquinavir, indinavir, ritonavir, n-docosanol, tromantadine and idoxuridine.

Anthelmintics such as mebendazole, thiabendazole, niclosamide, praziquantel, pyrantel embonate and diethylcarbamazine.

Cytotoxic agents such as plicamycin, cyclophosphamide, dacarbazine, fluorouracil and its prodrugs [described, for example, in International Journal of Pharmaceutics 111, 223-233 (1994)], methotrexate, procarbazine, 6-mercaptopurine and mucophenolic acid.

Metabolism

Anorectic and weight reducing agents including dexfenfluramine, fenfluramine, diethylpropion, mazindol and phentermine.

Agents used in hypercalcaemia such as calcitriol, dihydrotachysterol and their active derivatives or analogs.

Respiratory System

Antitussives such as ethylmorphine, dextromethorphan and pholcodine.

Expectorants such as acetylcysteine, bromhexine, emetine, guaiphenesin, ipecacuanha ans saponins.

Decongestants such as phenylephrine, phenylpropanolamine ans pseudoephedrine.

Bronchospasm relaxants such as ephedrine, fenoterol, orciprenaline, rimiterol, salbutamol, sodium cromoglycate, cromoglycic acid and its prodrugs [described, for example, in International Journal of Pharmaceutics 7, 63-75 (1980)], terbutaline, ipratropium bromide, salmeterol and theophylline and theophylline derivatives.

Allergy and Immune System

Antihistamines such as meclozine, cyclizine, chlorcyclizine, hydroxyzine, brompheniramine, chlorpheniramine, clemastine, cyproheptadine, dexchlorpheniramine, diphenhydramine, diphenylamine, doxylamine, mebhydrolin, pheniramine, tripolidine, azatadine, diphenylpyraline, methdilazine, terfenadine, astemizole, loratidine and cetirizine.

Local anaesthetics such as bupivacaine, amethocaine, lignocaine, cinchocaine, dibucaine, mepivacaine, prilocaine and etidocaine.

Stratum corneum lipids, such as ceramides, cholesterol and free fatty acids, for improved skin barrier repair [Man, et al. J. Invest. Dermatol., 106(5), 1096, 1996].

Neuromuscular blocking agents such as suxamethonium, alcuronium, pancuronium, atracurium, gallamine, tubocurarine and vecuronium.

Smoking cessation agents such as nicotine, bupropion and ibogaine.

Insecticides and other pesticides which are suitable for local or systemic application.

Dermatological agents, such as vitamins A and E, vitamin E acetate and vitamin E sorbate.

Allergens for desensitisation such as house dust mite allergen.

Nutritional agents, such as vitamins, essential amino acids and essential fats.

Keratolytics such as the alpha-hydroxy acids, glycollic acid and salicylic acid.

Psychicenergisers, such as 3-(2-aminopropyl)indole, 3-(2-aminobutyl)indole, and the like.

Anti-acne agents such as containing isotretinoin, tretinoin and benzoyl peroxide.

Anti-psoriasis agents such as containing etretinate, cyclosporin and calcipotriol.

Anti-itch agents such as capsaicin and its derivatives such as nonivamide [Tsai, et al. Drug. Dev. Ind. Pharm., 20(4), 719, 1994].

Anticholinergic agents, which are effective for the inhibition of axillary sweating and for the control of prickly heat. The antiperspirrant activity of agents such as methatropine nitrate, propantheline bromide, scopolamine, methscopolamine bromide, and the new class of soft antiperspirants, quaternary acyloxymethyl ammonium salts [described, for example, by Bodor et al, J. Med. chem. 23, 474 (1980) and also in United Kingdom Specification No. 2010270, published Jun. 27, 1979].

Other physiologically active peptides and proteins, small to medium-sized peptides, e.g., vasopressin and human growth hormone.

Whilst it is preferred that the active agent and penetration enhancer be delivered by simultaneous administration, the penetration enhancer may be applied before or after the application of the physiologically active agent, if desired.

The present invention also provides a transdermal drug delivery system which comprises at least one physiologically active agent or prodrug thereof, at least one dermal penetration enhancer and at least one volatile liquid; characterised in that the dermal penetration enhancer is a safe skin-tolerant ester sunscreen.

According to a second aspect of the present invention there is provided a non-occlusive, percutaneous or transdermal drug delivery system which comprises:

(i) an effective amount of at least one physiologically active agent or prodrug thereof;

(ii) at least one non-volatile dermal penetration enhancer; and (iii) at least one volatile liquid; characterised in that the dermal penetration enhancer is adapted to transport the physiologically active agent across a dermal surface or mucosal membrane of an animal, including a human, when the volatile liquid evaporates, to form a reservoir or depot of a mixture comprising the penetration enhancer and the physiologically active agent or prodrug within said surface or membrane; and the dermal penetration enhancer is of low toxicity to, and is tolerated by, the dermal surface or mucosal membrane of the animal.

The present invention also provides a method for administering at least one systemic or locally acting physiologically active agent or prodrug thereof to a animal which comprises applying an effective amount of the physiologically active agent in the form of a drug delivery system according to the present invention.

Furthermore, the present invention provides a method for the treatment or prophylaxis of a disease or condition in a animal which comprises administering to a dermal surface or mucosal membrane of said animal in need of such treatment a therapeutically effective amount of a drug delivery system according to the present invention.

The invention further provides apparatus for the controlled application of an aerosol or spray composition to the dermal surface or mucosal membrane of an animal, which comprises a shroud as described hereinafter.

Preferably the animal is a human but the invention also extends to the treatment of non-human animals.

Preferably the non-occlusive drug delivery system is not supersaturated with respect to the physiologically active agent or prodrug. As the volatile liquid of the non-occlusive drug delivery system evaporates, the resulting non-volatile composition is rapidly driven into the dermal surface or mucosal membrane. It is possible that as the volatile liquid evaporates, the non-volatile dermal penetration enhancer becomes supersaturated with respect to the active agent. However, it is preferred that any supersaturation does not occur before transport of the resulting non-volatile composition across the epidermal surface has occurred.

It is most desirable that, after application of the non-occlusive, percutaneous or transdermal drug delivery system, the volatile component of the delivery system evaporates and the area of skin to which the drug delivery system was applied becomes touch-dry. Preferably said area of skin becomes touch-dry within 10 minutes, more preferably within 3 minutes, most preferably within 1 minute.

The group of dermal penetration enhancing ester sunscreen compounds of the present invention are particularly suitable for non-occlusive transdermal delivery of active agents through the skin and membranes of a animal. These dermal penetration enhancing compounds are of low toxicity to the skin and are excellent promoters of percutaneous and oral mucosal (especially gingival) absorption. In addition to the dermal penetration enhancers of the present invention, known dermal penetration enhancers may be employed in the non-occlusive transdermal drug delivery system of the present invention. These known dermal penetration enhancers include laurocapram (Azone®) and laurocapram derivatives, such as those 1-alkylazacycloheptan-2-ones specified in U.S. Pat. No. 5,196,410, and oleic acid and its ester derivatives, such as methyl, ethyl, propyl, isopropyl, butyl, vinyl and glycerylmonooleate, and sorbitan esters such as sorbitan monolaurate and sorbitan monooleate, and other fatty acid esters such as isopropyl laurate, isopropyl myristate, isopropyl palmitate, diisopropyl adipate, propylene glycol monolaurate and propylene glycol monooleate, and long chain alkyl esters of 2-pyrrolidone, particularly the 1-lauryl, 1-hexyl and 1-(2-ethylhexyl) esters of 2-pyrollidene and those dermal penetration enhancers given in U.S. Pat. No. 5,082,866, particulary dodecyl (N,N-dimethylamino) acetate and dodecyl (N,N-dimethylamino) propionate and in U.S. Pat. No. 4,861,764, particularly 2-n-nonyl-1-3-dioxolane.

Preferred known dermal penetration enhancers are laurocapram and laurocapram derivatives, such as those 1-alkylazacycloheptan-2-ones specified in U.S. Pat. No. 5,196,410, and oleic acid and its ester derivatives, such as methyl, ethyl, propyl, isopropyl, butyl, vinyl and glycerylmonooleate, and those given in U.S. Pat. No. 5,082,866, particularly dodecyl (N,N-dimethylamino) acetate and dodecyl (N,N-dimethylamino) propionate and in U.S. Pat. No. 4,861,764, particularly 2-n-nonyl-1-3-dioxolane. Most preferred known dermal penetration enhancers are oleic acid and its ester derivatives, such as methyl, ethyl, propyl, isopropyl, butyl, vinyl and glycerylmonooleate, and those given in U.S. Pat. No. 5,082,866, particulary dodecyl (N,N-dimethylamino) acetate and dodecyl (N,N-dimethylamino) propionate and in U.S. Pat. No. 4,861,764, particularly 2-n-nonyl-1-3-dioxolane.

Preferred volatile liquids of the present invention include safe skin-tolerant solvents such as ethanol and isopropanol. An aerosol propellant, such as dimethyl ether, may constitute a volatile liquid for the purpose of the present invention.

Surprisingly the group of dermal penetration compounds identified enhance the absorption of active agents and pro-drugs thereof through the skin and mucous membranes while avoiding the significant pharmacological disadvantages and toxicities of prior art enhancers. Additionally, the group of compounds of the invention surprisingly exhibit appreciable penetration into and substantivity for the outer layers of the skin, namely the stratum corneum which has previously presented a formidable barrier to percutaneous drug absorption.

In drug delivery systems according to the first aspect of the present invention a pharmaceutical compounding agent, co-solvent, surfactant, emulsifier, antioxidant, preservative, stabiliser, diluent or a mixture of two or more of said components may be incorporated in these systems as is appropriate to the particular route of administration and dosage form. The amount and type of components used should be compatible with the dermal penetration enhancers of this invention as well as with the active ingredient. A co-solvent or other standard adjuvant, such as a surfactant, may be required to maintain the agent in solution or suspension at the desired concentration.

The pharmaceutical compounding agents can include paraffin oils, esters such as isopropyl myristate, ethanol, silicone oils and vegetable oils. These are preferably used in the range 1 to 50%. Surfactants such as ethoxylated fatty alcohols, glycerol mono stearate, phosphate esters, and other commonly used emulsifiers and surfactants preferably in the range of 0.1 to 10% may be used, as may be preservatives such as hydroxybenzoate esters for preservation of the compound preferably in amounts of 0.01% to 0.5%. Typical co-solvents and adjuvants may be ethyl alcohol, isopropyl alcohol, acetone, dimethyl ether and glycol ethers such as diethylene glycol mono ethyl ether. These may be used in amounts of 1 to 50%.

In drug delivery systems according to the second aspect of the present invention, whilst a pharmaceutical compounding agent, co-solvent, surfactant, emulsifier, antioxidant, preservative, stabiliser, diluent or a mixture of two or more of said components may be incorporated, these must be compatible with the ability of the system to become touch-dry after application.

Because of the effect of the penetration enhancer of the invention, the dosage of the physiologically active agent may often be less than that conventionally used. It is proposed that, a dosage near the lower end of the useful range of the particular agent may be employed initially and increased as indicated from the observed response if necessary.

The concentration of physiologically active agent used in the drug delivery system will depend on its properties and may be equivalent to that normally utilised for the particular agent in conventional formulations. Both the amount of physiologically active agent and the amount of penetration enhancer will be influenced by the type of effect desired. For example, if a more localised effect is required in treating a superficial infection with an antibacterial agent, lower amounts of physiologically active agents and lower concentrations of enhancer may be appropriate. Where deeper penetration is desired, as in the case of local anaesthesia, a higher concentration of enhancer may be appropriate.

Where it is desired to achieve systemic concentration of an agent, proportionately higher concentrations of the enhancer of the invention may be required in the transdermal drug delivery system of the present invention, and the amount of active substance included in the composition should be sufficient to provide the blood level desired.

The concentration of absorption/penetration enhancer may be in the range from 10-10,000 weight percent of absorption/penetration enhancer based upon the weight of active ingredient. The ratio of penetration enhancer to active ingredient may vary considerably and will be governed as much as anything, by the pharmacological results that are required to be achieved. In principle, it is desirable that as little absorption enhancer as possible is used. On the other hand, for some actives, it may well be that the upper range of 10,000% by weight will be required. It is preferred that the penetration enhancer and active are in approximately equal proportions.

Surprisingly, it has been found that a large range of systemic drugs can be delivered to a subject in need thereof by the non-occlusive drug delivery system and methods of the present invention. That is, the drug delivery system delivers the physiologically active agent to a animal without the need for an occlusive patch device. The efficacy of known systemic drug delivery systems, and in particular transdermal patch devices is maintained, and in some cases is increased by use of non-occlusive, percutaneous or transdermal drug delivery systems of the present invention.

A particular advantage of the non-occlusive drug delivery system of the present invention is that patient compliance is improved as the system does not occlude the skin or membrane and therefore local irritation and allergic sensitisation problems arising from prolonged exposure of the skin to both the delivery system of occlusive transdermal patch devices and the adhesive used to affix these patches to the skin are reduced.

The following definitions apply through this description and the claims which follow.

The term "mucous membrane" refers generally to any of the mucous membranes in the body, absorption through the mucous membranes of the oral cavity which is of particular interest. Thus, buccal, sublingual, gingival and palatal absorption are specifically contemplated by the present invention. In a preferred embodiment, the penetration enhancers of the present invention are used to improve absorption through those oral tissues which most resemble the skin in their cellular structure, i.e. the gingiva and palate.

The term "physiologically active agent" is used herein to refer to a broad class of useful chemical and therapeutic agents.

The term "physiologically active" in describing the agents contemplated herein is used in a broad sense to comprehend not only agents having a direct pharmacological effect on the host, but also those having an indirect or observable effect which is useful in the medical arts.

A "prodrug" of a physiologically active agent herein means a structurally related compound or derivative of an active compound which in the animal body is converted to the desired physiologically active compound. The prodrug itself may have little or none of the desired activity.

The terms "percutaneous" and "transdermal" are used herein in the broadest sense to refer to being able to pass through unbroken skin.

The term "dermal penetration enhancer" is used herein in its broadest sense to refer to an agent which improves the rate of percutaneous transport of active agents across the skin for use and delivery of active agents to organisms such as animals, whether it be for local application or systemic delivery.

The term "non-occlusive" is used herein in its broadest sense to refer to not trapping or closing the skin to the atmosphere by means of a patch device, fixed reservoir, application chamber, tape, bandage, sticking plaster, or the like which remains on the skin at the site of application for a prolonged length of time.

The term "stratum corneum" is used herein in its broadest sense to refer to the outer layer of the skin, which is comprised of (approximately 15) layers of terminally differentiated keratinocytes made primarily of the proteinaceous material keratin arranged in a 'brick and mortar' fashion with the mortar being comprised of a lipid matrix made primarily from cholesterol, ceramides and long chain fatty acids. The stratum corneum creates the rate-limiting barrier for diffusion of the active agent across the skin.

The term "skin-depot" is used herein in its broadest sense to refer to a reservoir or deposit of active agent and dermal penetration enhancer within the stratum corneum, whether it be intra-cellular (within keratinocytes) or inter-cellular.

The term "volatile:non-volatile liquid vehicle" is used in the art to refer to a liquid pharmaceutical vehicle comprising a volatile liquid mixed with a non-volatile liquid vehicle, such as a dermal penetration enhancer. A system or vehicle comprising a volatile liquid mixed with a non-volatile dermal penetration enhancer when described herein is used in its broadest sense to include those systems known as volatile: non-volatile liquid vehicles.

Alkyl and alkoxy groups referred to herein may be either straight chain or branched. The term "lower alkyl" means alkyl groups containing from 1 to 5 carbon atoms. The term "lower alkoxy has a similar meaning. The term "long chain alkyl" means alkyl groups containing from 5 to 18 carbon atoms, more preferably 6 to 18 carbon atoms. The term "halide" means fluoride, chloride, bromide or iodide. The term "heterocyclic ring" is herein defined to mean a ring of carbon atoms containing at least one hetero atom, and further the ring may be saturated or unsaturated to any allowable degree.

The term "sunscreen" is used herein in its broadest sense to refer to a chemical agent capable of filtering out ultraviolet light.

The non-occlusive, percutaneous or transdermal drug delivery system of the present invention enables a wide range of physiologically active agents to be delivered through the skin to achieve a desired systemic effect. The drug delivery system preferably comprises the active agent intimately mixed with a non-volatile dermal penetration enhancer and a volatile liquid. Where the drug delivery system is applied to the skin, the active agent and non-volatile liquid are thermodynamically driven into the skin as the volatile liquid evaporates. Once within the skin the non-volatile liquid may either disrupt the lipid matrix and/or act as a solubilizer to allow an enhanced penetration rate of the active agent through the skin and into the subject being treated. In this way, the dermal penetration enhancer acts as a vehicle and many systemic active agents are able to be transdermally administered to an animal.

It is believed that the non-volatile dermal penetration enhancer is readily absorbed into the stratum corneum in sufficient quantities to form a reservoir or depot of the dermal penetration enhancer within the stratum corneum. The dermal penetration enhancer also contains the active agent to be administered and as the dermal penetration enhancer crosses through the skin to form the skin-depot, the active agent contained therein is transported through the skin and contained within the depot. These depots are believed to form within the lipid matrix of the stratum corneum wherein the lipid matrix creates a rate-limiting barrier for diffusion of the active agent across the skin and allows the dermally administered active agent to be systemically released over a period of time, usually up to 24 hours.

Once the volatile liquid of the non-occlusive drug delivery system has evaporated, driving the mixture of non-volatile dermal penetration enhancer and active agent into the stratum corneum, the outer surface of the skin is then substantially free of active agent and non-volatile dermal penetration enhancer. Normal touching, wearing of clothes, rinsing or even washing of the skin will not, to any significant extent, affect delivery of the drug or displace either the active agent or the non-volatile dermal penetration enhancer, once the volatile liquid has evaporated.

This is in contrast to prior-art systems where supersaturated solutions are used to increase the rate of drug permeation across the skin. Such supersaturated solutions are susceptible to ready precipitation and require stabilization, such as with polymers, or protection from external surfaces or objects which may effect nucleation.

The rate of absorption of the physiologically active agent via the stratum corneum is increased by the non-volatile dermal penetration enhancer. The active agent may be dissolved or suspended in the dermal penetration enhancer at the time when it is being transported from the surface of the skin and into the stratum corneum. The performance of the dermal penetration enhancer to deliver a desired active agent varies with differences in both the nature of the dermal penetration enhancer and active agent. It is understood that different dermal penetration enhancers may need to be selected to be appropriate for delivery of various active agents.

Physiologically active agents that may be used in the percutaneous or transdermal drug delivery system of the present invention include any locally or systemically active agents which are compatible with the non-volatile dermal penetration enhancers and volatile liquids of the present invention and which can be delivered through the skin with the assistance of the dermal penetration enhancer to achieve a desired effect.

Preferred active agents include steroids and other hormone derivatives, more preferably testosterone, oestradiol, ethinyloestradiol, progesterone, norethisterone acetate and gestodene; and non-steroidal anti-inflammatory drugs, preferably ibuprofen, ketoprofen, flurbiprofen, naproxen and diclofenac; and opioid analgesics, preferably fentanyl and buprenorphine; and antinauseants, preferably prochlorperazine, metochlopramide, ondansetron and scopolamine; and antioestrogens, preferably tamoxifen and epitiostanol and the aromatase inhibitors, preferably exemestane and 4-hydroxy-androstenedione and its derivatives; and 5-alpha reductase inhibitors, preferably finasteride, turosteride, LY191704 and MK-306; and anxiolytics, preferably alprazolam; and prostaglandins, preferably alprostadil and prostacylcin and their derivatives; and melatonin; and anti-virals, preferably n-docosanol, tromantadine and lipophilic pro-drugs of acyclovir; and low molecular weight heparin, preferably enoxaparin; and anti-migraine compounds, preferably sumatriptan; and antihypertensives, preferably clonidine, amlodipine and nitrendipine; and anti-malarials, preferably primaquine; and minoxidil and minoxidil pro-drugs; and pilocarpine; and bronchodilators, preferably salbutamol, terbutaline, salmeterol; and anti-depressants, preferably ibogaine, bupropion and rolipram; and anti-alzheimer's agents, preferably fluphenazine and haloperidol; and anti-parkinson agents, preferably N-0923; and antiandrogens, preferably cyproterone acetate; and anorectic agents, preferably mazindol.

Diseases or conditions that may be treated by using the drug delivery system and methods of the present invention include, but are not limited to, male hormone replacement in testosterone deficient hypogonadal men, female hormone replacement therapy for postmenopausal women, androgen replacement therapy for females lacking libido, male contraception, female contraception, soft tissue injury, narcotic withdrawal, severe post-operative pain, motion sickness, oestrogen dependent breast cancer, prostatic enlargement and/or prostatic cancer, alopecia and acne, anxiety disorders, male impotence, Raynauds syndrome and varicose veins, sleep disorders such as jetlag, herpes virus infections, deep vein thrombosis, migraine, high blood pressure, malaria, diagnosis of cystic fibrosis and asthma, particularly nocturnal asthma, smoking cessation, psychotic disorders, severe post-natal depression, virilisation and obesity.

The foregoing lists are by no means intended to be exhaustive and any physiologically active agent that is compatible with the preferred volatile liquids and non-volatile dermal penetration enhancers of the drug delivery system may be applied by the method of the present invention to treat any appropriate disease or condition.

The drug delivery system of the present invention may be applied to the skin by means of an aerosol, spray, pump-pack, brush, swab, or other applicator. Preferably, the applicator provides either a fixed or variable metered dose application such as a metered dose aerosol, a stored-energy metered dose pump or a manual metered dose pump. The application is most preferably performed by means of a topical metered dose aerosol combined with an actuator nozzle shroud which together accurately control the amount and/or uniformity of the dose applied. One function of the shroud is to keep the nozzle at a pre-determined height above, and perpendicular to, the skin or membrane to which the drug delivery system is being applied. This function may also be achieved by means of a spacer-bar or the like. Another function of the shroud is to enclose the area above the skin or membrane in order to prevent or limit bounce-back and/or loss of the drug delivery system to the surrounding environment. Preferably the area of application defined by the shroud is substantially circular in shape.

The drug delivery system may be propelled by either pump pack or more preferably by the use of propellants such as hydrocarbons, hydro fluorocarbons, nitrogen, nitrous oxide, carbon dioxide or ethers, preferably dimethyl ether. The non-occlusive, drug delivery system is preferably in a single phase system as this allows less complicated manufacture and ease of dose uniformity. It may also be necessary to apply a number of dosages on untreated skin to obtain the desired result.

The invention will now be described with reference to the following examples and accompanying drawings. The examples and drawings are not to be construed as limiting the invention in any way. They are included to further illustrate the present invention and advantages thereof.

Figure 7:
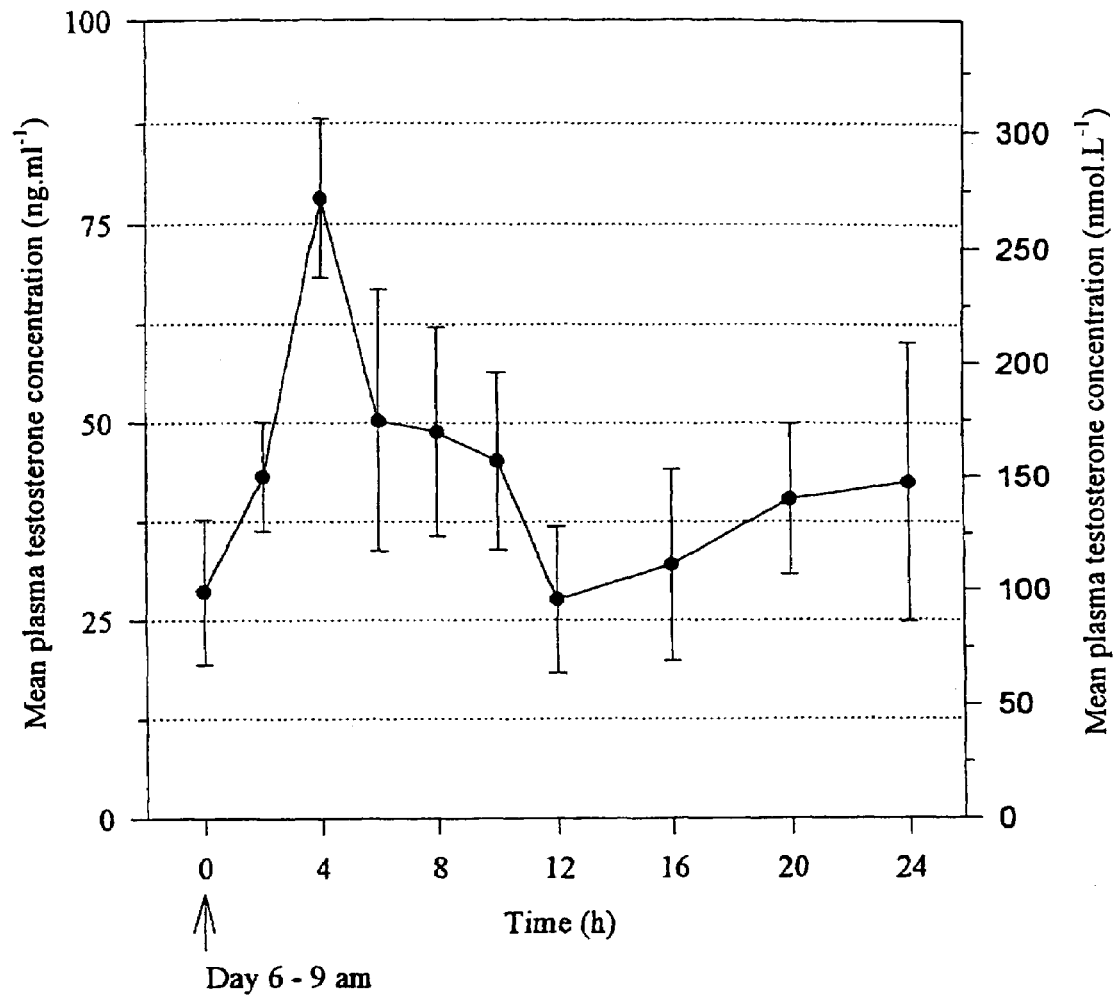

FIG. 7 is a graphical representation showing the plasma profile of testosterone in castrated domestic weanling pigs after the sixth once daily application of a metered dose topical aerosol. Each point represents the mean of 4 individual values and the error bars represent standard error of the mean. Testosterone levels shown are baseline subtracted and the mean baseline (±sem) on Day 1 at 0 h was 0.8 ng.ml$^{-1}$±0.3 ng.ml$^{-1}$.

Figure 8:
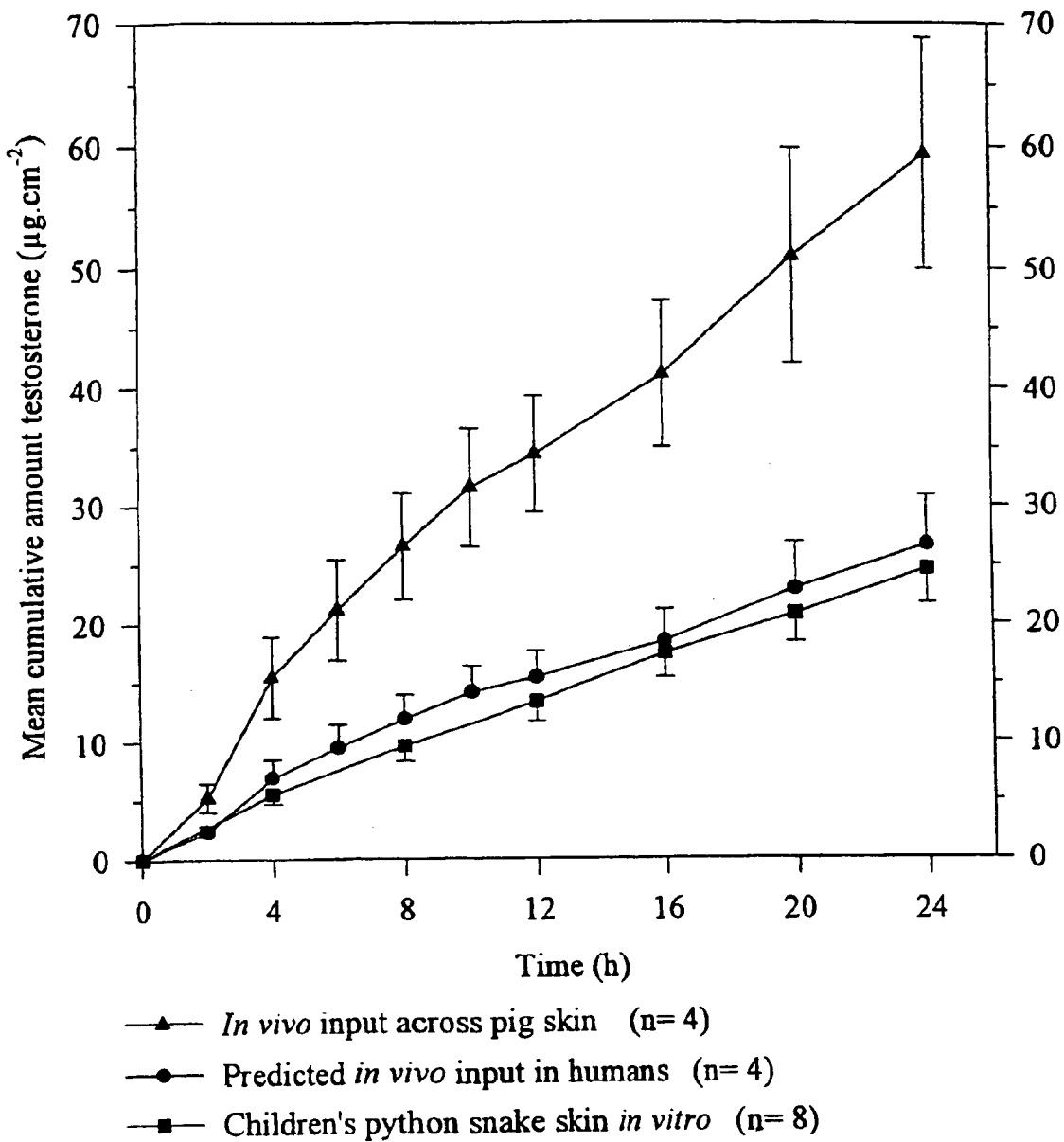

FIG. 8 is a graphical representation showing the predicted testosterone input across human skin in vivo and children's python snake skin in vitro. Error bars represent standard error of the mean.

Figure 9:
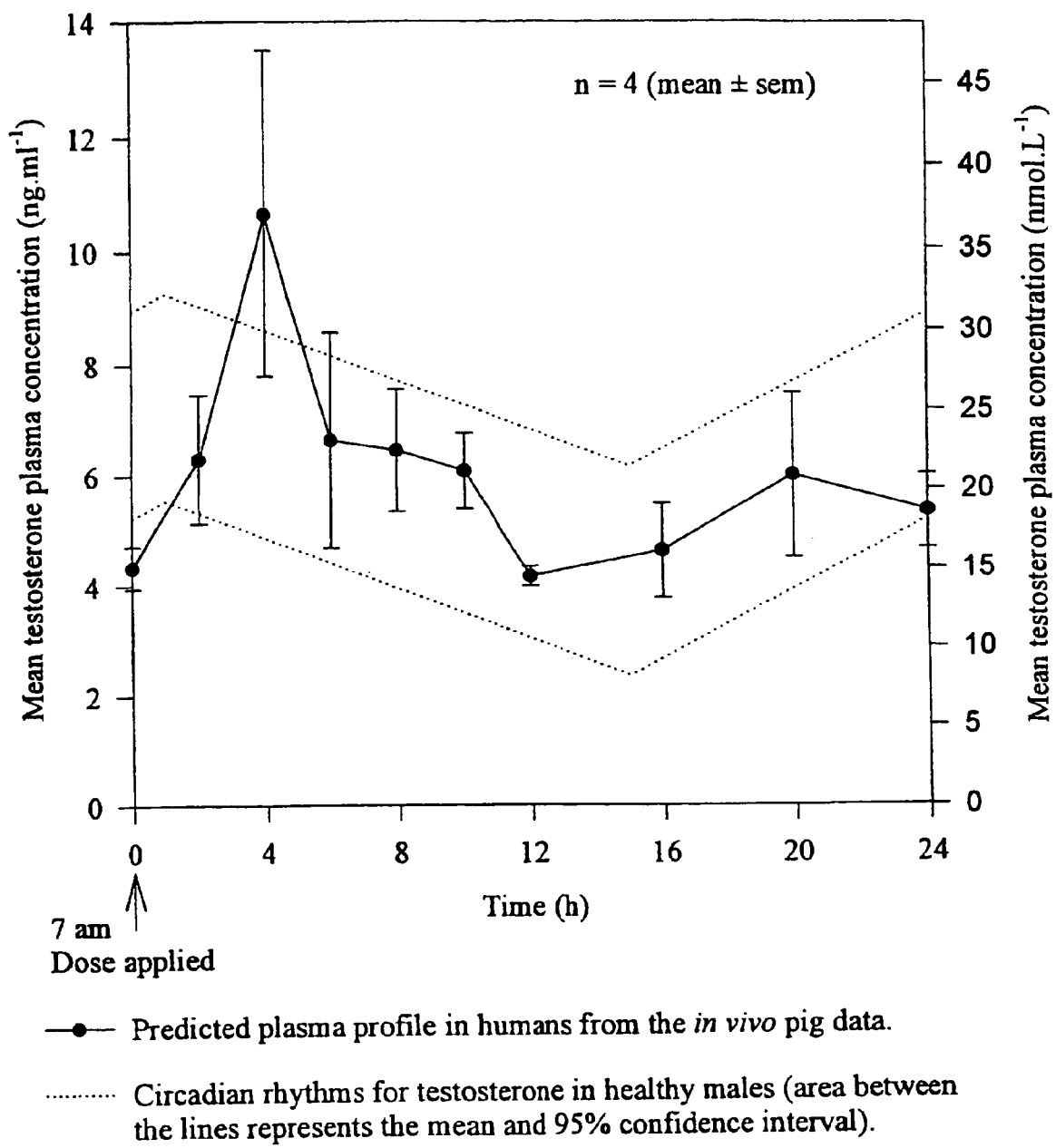

FIG. 9 is a graphical representation showing the predicted testosterone plasma concentration in hypogonadal males after once daily dosing to steady-state with a metered dose topical spray.

In the examples, the effectiveness of the penetration enhancers are illustrated by measuring the skin penetration of formulations of a number of representative physiologically active agents with the dermal penetration enhancers. Also, the skin penetration of physiologically active agents was measured with other prior art penetration enhancers as well as formulations of the physiologically active agents with common adjuvants, which serve as control formulations. The comparisons made generally consisted of measuring the relative penetration through shed snake skin of the various formulations. In every case, those formulations which contained the dermal penetration enhancers delivered more of the active agent through the skin than did the corresponding control formulation or commercial preparation.

In Vitro Skin Diffusion Measurements

Shed Snake Skin

The Children's python shed snake skin was obtained during natural shedding and the dorsal skin was used. Shed snake skin has shown to be a suitable model membrane for human skin by Itoh, et al., Use of Shed Snake Skin as a Model Membrane for In Vitro Percutaneous Penetration Studies: Comparison with Human Skin, Pharm. Res., 7(10), 1042-1047, 1990; and Rigg, et al., Shed Snake Skin and Hairless Mouse Skin as Model Membranes for Human Skin During Permeation Studies, J. Invest. Dermatol., 94; 235-240, 1990.

Full Thickness Skin

The animals used in these investigations were obtained from the animal house at the Victorian College of Pharmacy, Monash University, Parkville, Australia.

a. Hairless Mouse Skin

Hairless mice of 4-8 weeks of age were used. The mouse skin was excised and full-thickness skin was isolated from the torso, the subcutaneous fat and connective tissue removed and the skin cut into circles of 2.0 cm$^2$, then placed into the diffusion cells for flux measurements.

b. Guinea Pig Skin

Adult guinea pigs of either sex (weight range 500 g-750 g) were used. The hair on the back flank and back was removed with the aid of depilatory wax (Arielle®) under halothane anaesthesia. Seven days later, after the stratum corneum had completely regenerated, the guinea pigs were killed and the skin removed and placed on a chilled slab. The subcutaneous fat and connective tissue removed and the skin cut into circles and then placed into the diffusion cells for flux measurements. For in vivo experiments the guinea pigs were housed in individual cages and the topical hydroquinone formulations were applied to the hair-free areas. Each guinea pig received the test or control formulation on the corresponding contralateral site, thus allowing each animal to act as its own control.

In Vitro Skin Diffusion Experiments in Franz-Type Cells

The work using Hydroquinone was performed using vertical Franz diffusion cells which had an effective diffusional area of 1.3 cm$^2$, a receiver chamber temperature of 37 or 32 degrees Celsius and receiver chamber volume of 13 mL of normal saline.

In Vitro Skin Diffusion Experiments in Horizontal Diffusion Cells

Figure 1:
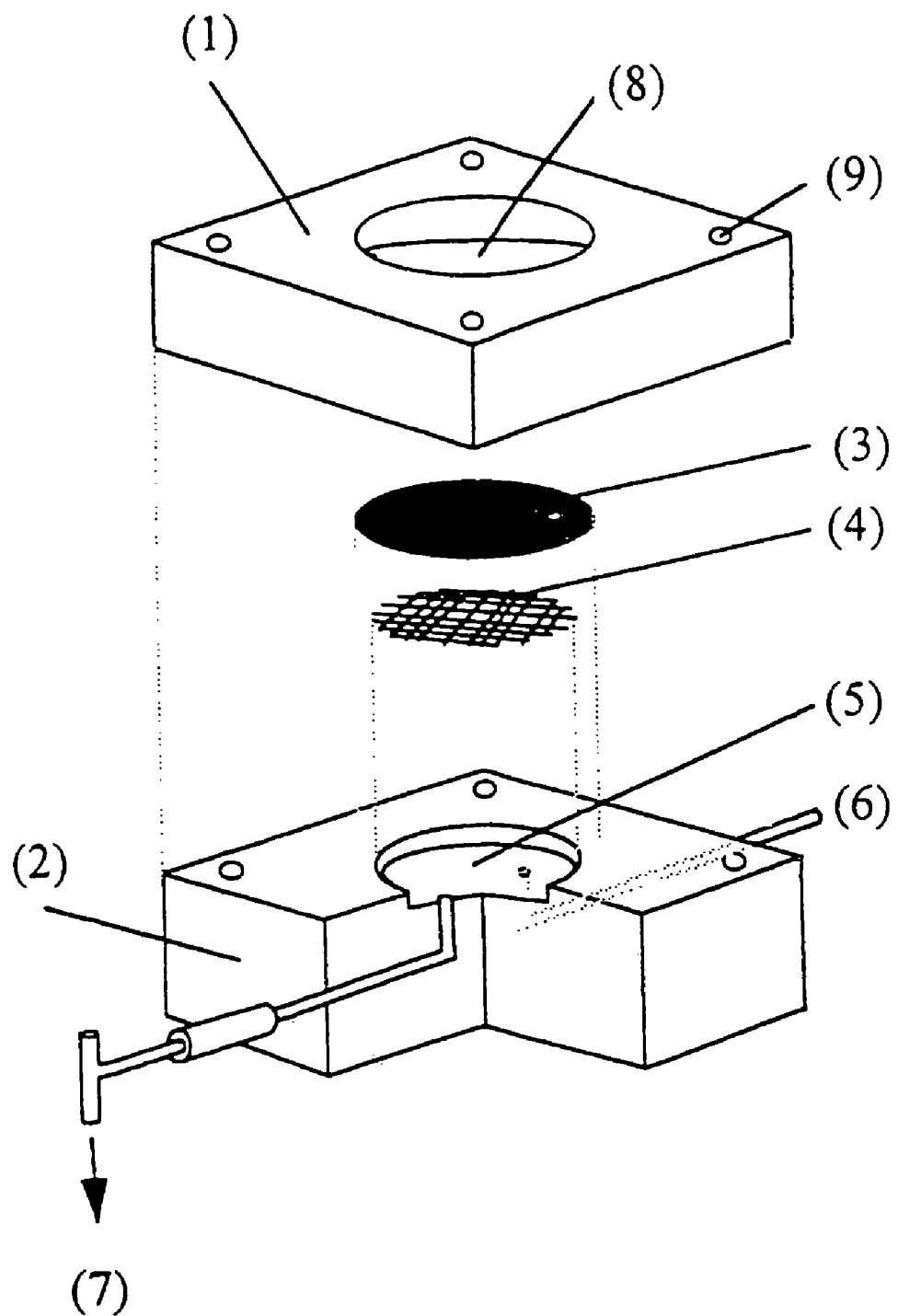
FIG. 1 is a diagrammatic representation showing the halves of a stainless steel flow-through diffusion cell.

A modified stainless steel flow-through diffusion cell assembly based on that first shown by Cooper in J. Pharm. Sci. 73(8), 1984, was used to perform the experiments on diffusion of the drugs from various donor compositions through the skin (either snake or hairless mouse). The flow-through diffusion cell used to perform the present experiments is shown in FIG. 1. The cell consists of an upper section (1) and a lower section (2). A stainless steel wire mesh support (4) is housed in a recess (5) in the lower section of the cell. The skin sample (3), cut into a circle, is gently placed over the support (4) and the two sections (1, 2) of the cells are secured together by screws (not shown), using the locating holes (9), to form a tight seal. An aperture (8) in the upper section of the cell, which has an area of 0.79 cm$^2$ (0.5 cm in diameter) forms a well above the skin into which the topical formulation is applied. In most cases 400 microL of formulation, solution or suspension containing the drug substance to be tested was applied evenly over the skin. The bottom section of the cell is provided with inlet (6) and outlet (7) tubes which connect to the bottom of the recess (5) and through which a receptor solution was pumped by a microcassette peristaltic pump (Watson Marlow, UK) (not shown) at a constant flow rate to maintain sink conditions. The receptor solution consisted of 50% propylene glycol in water, made isotonic with 0.9% sodium chloride and preserved with 0.1% sodium azide or 0.1% sodium fluoride. To prevent air bubbles forming under the skin, the wire mesh (4) ensures turbulent receptor flow. The recess (5) is filled with receptor solution prior to placing the skin in the cell. The receptor solution was degassed by spraying the solution into fine droplets under vacuum while stirring at 40° C. Degassing was repeated three times. These precautions eliminated the need for a bubble chamber in the diffusion cell. The diffusion cells were set on a hollow metal heater bar which maintained normal skin temperature of 32° C. (±0.5° C.) means of heated, circulating water (Thermomix, Braun, Germany). Each diffusion cell had its receptor solution collected via tube (7) into polyethylene vials (6 ml liquid scintillation vials, Packard instruments, Netherlands) at two or four hour intervals for 24 hours, by means of an automated rotating fraction collector (Retriever II, ISCO, Australia). The amount of drug in each vial containing receptor solution was determined by reverse phase HPLC. Prior to analysis each vial was weighed with an analytical balance (Mettler AT261, Australia) and the volume calculated from the density of the receptor solution which was 1.0554 g/cm$^3$ at 22° C.

The concentration of applied drug in each diffusion cell sample was measured using high pressure liquid chromatography (HPLC). The receptor solution was assayed neat, with 20 microL injected (WISP 712 autoinjector, Waters, Australia) into a freshly prepared and degassed (by filtering) mobile phase. Each drug was separated using a pre column fitted with a C18 insert and a μBandapak C18 (30 cm×3.9 nm) HPLC column (Waters). Absorbance was measured at the appropriate wavelength using a Waters tuneable absorbance detector and peak area was plotted and integrated using a Shimadzu C-R3A chromatopac integrator. The results reported for each experiment are the average values of four replicate diffusion cells unless stated otherwise. The assay conditions used for each different drug are given in each example.

EXAMPLE 1

Figure 2:
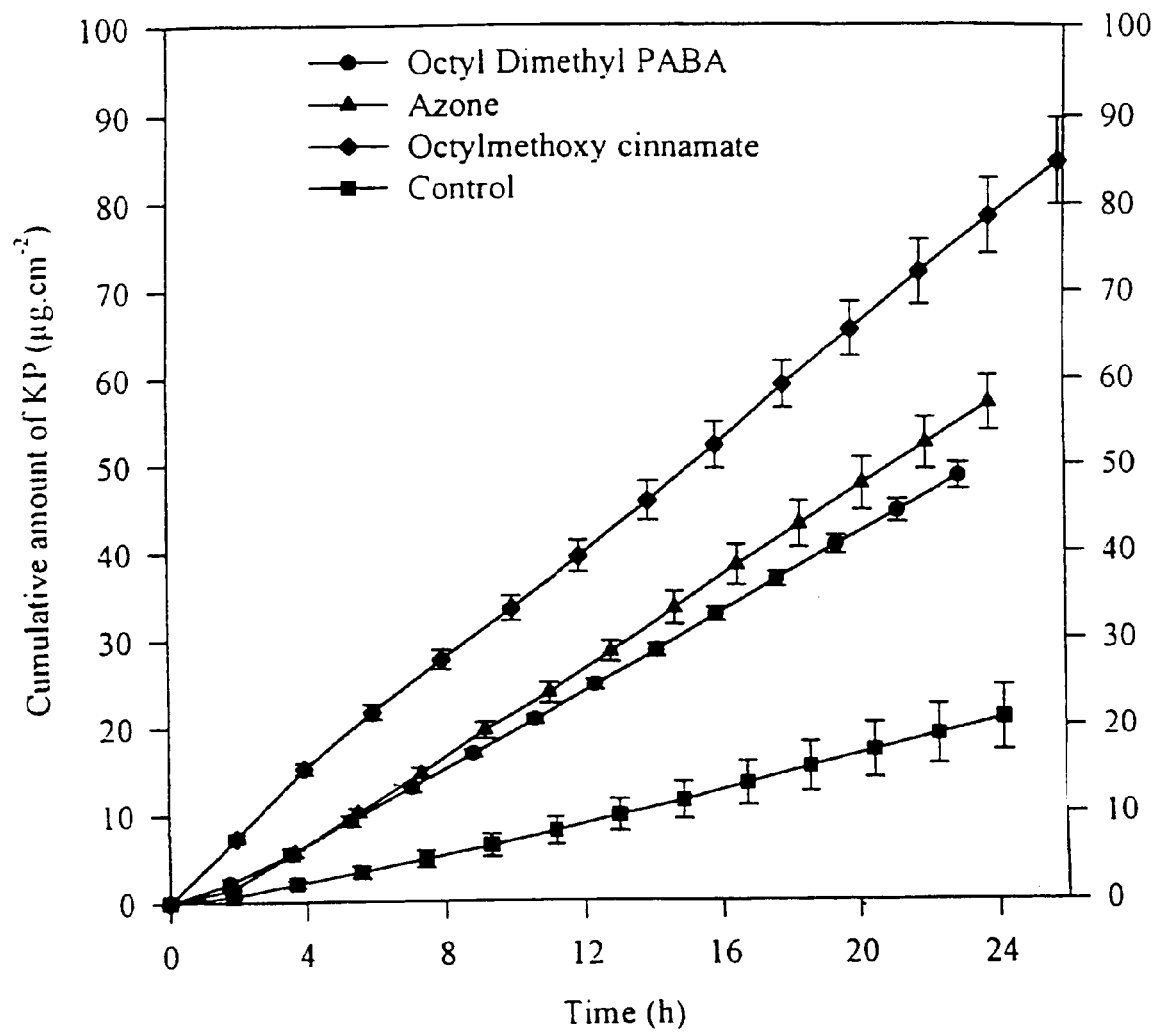
FIG. 2 is a graphical representation showing the effect of pretreatment with various enhancers on the diffusion of ketoprofen across shed snake skin.

The in vitro diffusion cell method described above was used to compare the penetration of 400 microL of 2% w/v ketoprofen in 70% v/v aqueous ethanol applied to the shed snake skin following the application of 400 microL of the different dermal penetration enhancers in a 2% v/v solution in 70% ethanol, 2 hours prior to the application of the ketoprofen. The control experiment involved application of 400 microL of 70% aqueous ethanol alone for 2 hours, followed by application of 400 microL of the 2% ketoprofen solution. Samples were assayed according to the method described previously. The detection wavelength was 255 nm and the mobile phase consisted of acetonitrile:water (55:45) made to pH 3·0 with orthophosphoric acid (BDH, Australia). Table 1 shows the mean flux of ketoprofen across the snake skin over 24 hours as determined by the linear regression of the cumulative amount of ketoprofen crossing the skin versus time (Units=microg/cm$^2$.h). FIG. 2 shows the representative mean cumulative amount versus time plots for ketoprofen.

TABLE 1

| Enhancer type | Mean flux +/− std error (microg/cm$^2$ · h) | p value relative to control | Enhancement ratio |
|---|---|---|---|
| Control - no enhancer, n = 9 | 0.96 ± 0.18 | — | — |
| Azone, n = 2 | 2.58 ± 0.23 | 0.0029 | 2.7 |
| Octyl dimethyl PABA, n = 3 | 2.25 ± 0.14 | 0.0068 | 2.3 |

TABLE 1-continued

| Enhancer type | Mean flux +/− std error (microg/cm² · h) | p value relative to control | Enhancement ratio |
|---|---|---|---|
| Octylmethoxy cinnamate, n = 3 | 3.22 ± 0.28 | 0.0003 | 3.35 |
| Octyl salicylate, n = 2 | 27.66 ± 5.26 | <0.0070 | 28.81 |

NB. Enhancement ratio = mean flux enhancer/mean flux control

Statistical significance was determined by means of a Student's t-test. Azone was selected as the standard penetration enhancer for comparison since it has been widely used in previous percutaneous penetration experiments.

EXAMPLE 2

The in vitro diffusion cell method described above was used to compare the penetration of 30 microL of the commercial formulation Indospray™ (Rhone-Poulenc Rorer, Australia), which is a 1.0% w/w solution of indomethacin in 95% v/v ethanol when applied to the snake skin. 10 microL of increasing concentrations of Octyl dimethyl PABA in absolute ethanol were applied 30 mins prior to the application of the indomethacin formulation. The control experiment involved application of 10 microL of absolute ethanol alone 30 mins prior to the application of the indomethacin formulation. Samples were assayed according to the method described previously. The detection wavelength was 254 nm and the mobile phase consisted of acetonitrile:water (55% v/v:45% v/v) made to pH 3.0 with orthophosphoric acid. Table 2 shows the mean flux of indomethacin across the snake skin over 24 hours.

TABLE 2

| Enhancer type | Enhancer conc. (% v/v) | Mean flux +/− std error (microg/cm² · h) | p value relative to control | Enhancement ratio |
|---|---|---|---|---|
| Control - no Enhancer | n/a | 1.24 ± 0.05 | — | — |
| Octyl dimethyl PABA | 1.6 | 1.43 ± 0.14 | ns | 1.2 |
| as above, n = 3 | 3.2 | 1.71 ± 0.32 | ns | 1.4 |
| as above | 6.4 | 1.94 ± 0.09 | 0.0005 | 1.6 | ns = not statistically significantly different

These results demonstrate the ability of the dermal penetration enhancers to be applied alone prior to exposure of the skin to the physiologically active ingredient(s) formulations without penetration enhancers. Enhancement of percutaneous absorption is extensive, as well as being dose-dependent in manner, such that the desired level of enhancement can be achieved by, utilising the appropriate dose of dermal penetration enhancer applied to the skin.

EXAMPLE 3

The same protocol as Example 1 was repeated, except the dermal penetration enhancers were included in the ketoprofen formulation, such that 400 microL of 2% w/v ketoprofen and 2% v/v dermal penetration enhancer in 70% v/v aqueous ethanol was applied to the skin from the start of the diffusion experiment.

Figure 3:
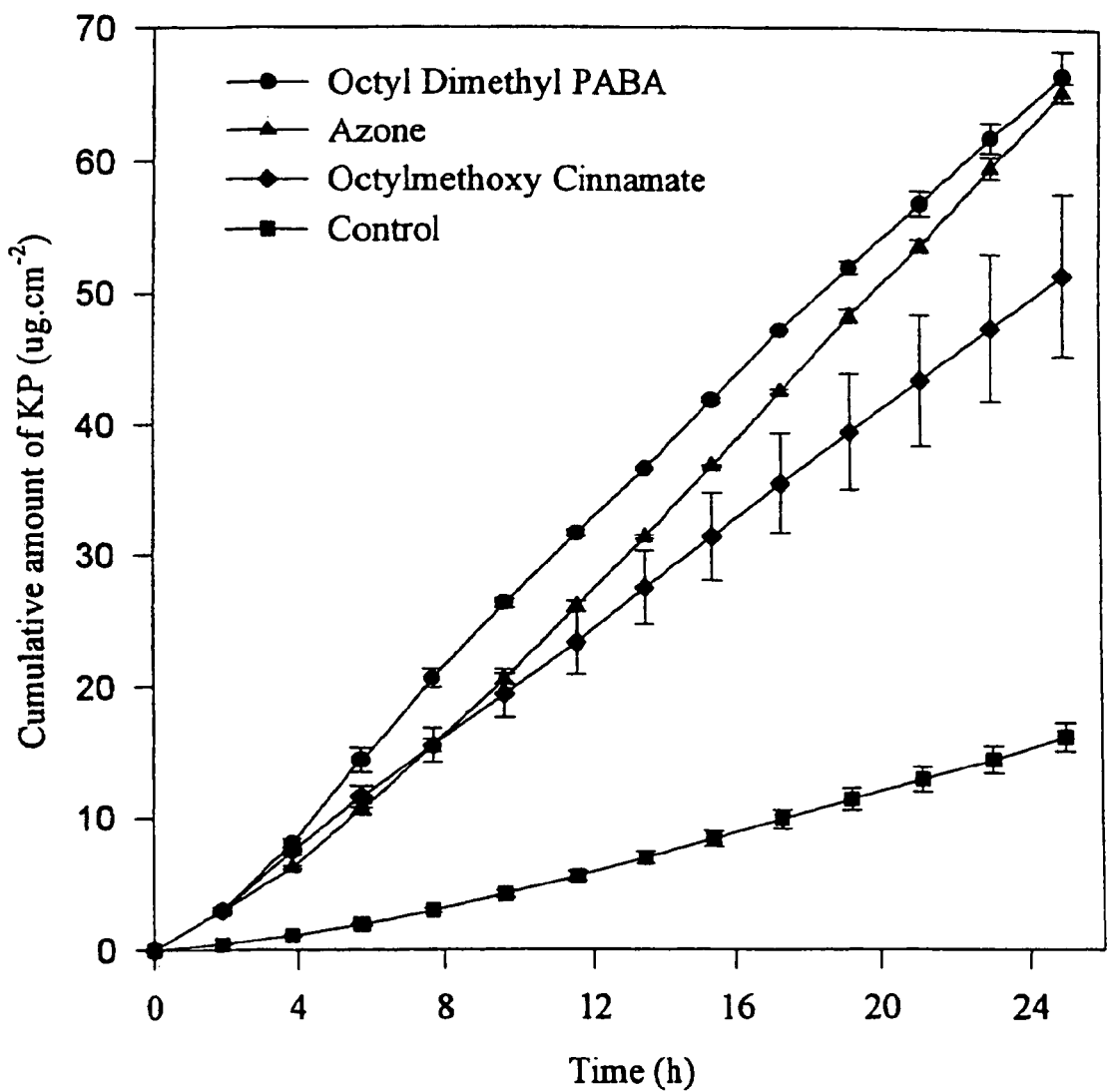
FIG. 3 is a graphical representation showing the effect of various enhancers on the diffusion of ketoprofen across shed snake skin.

Table 3 shows the mean flux of ketoprofen across the snake skin over 24 hours. FIG. 3 shows the representative mean cumulative amount versus time plots for ketoprofen.

TABLE 3

| Enhancer type | Mean flux +/− std error (microg/cm² · h) | p value relative to control | Enhancement ratio |
|---|---|---|---|
| Control - no enhancer, n = 10 | 0.78 ± 0.07 | — | — |
| Azone, n = 2 | 2.84 ± 0.11 | <0.0001 | 3.6 |
| Octyl dimethyl PABA, n = 2 | 2.71 ± 0.18 | <0.0001 | 3.5 |
| Octylmethoxy cinnamate, n = 2 | 2.08 ± 0.39 | 0.0413 | 2.7 |
| Octyl salicylate, n = 4 | 61.68 ± 14.89 | <0.0059 | 79.1 |

These results demonstrate the ability of the dermal penetration enhancers to be applied together with the physiologically active ingredient/s within the same formulation to achieve their percutaneous absorption enhancement.

EXAMPLE 4

Table 4 shows the mean flux (% dose/h)+/−the standard error of the mean of hydroquinone (HQ) penetrated across full-thickness guinea pig skin in vitro from a gel formulation applied to the skin at a dose of 15 mg/cm². Radio labelled hydroquinone (C14, Amersham) was added to each of the topical formulations. At specified time intervals 200 microL of receptor solution was withdrawn with a micro-pipette and replaced with 200 microL of fresh normal saline. The 200 microL samples were added to 800 microL of water which in turn was added to 10 mL of scintillation cocktail consisting of Toluene™ 1L, PPO 5g, POPOP 0.1 g and Triton X™ 500 mL. The scintillation counting was performed on a Packard Tricarb 460C instrument. Disintegrations per minute were determined by an external standard procedure and calculated by the data system of the instrument.

TABLE 4

| Enhancer type | Flux (% dose/h) | Enhancement ratio (enhancer/control) |
|---|---|---|
| PARSOL ® MCX 3% v/v | 0.93 ± 0.19* | 2.7 |
| ESCALOL ® 507 3% v/v | 1.02 ± 0.09* | 2.9 |
| AZONE 5% v/v, PARSOL ® MCX 3% v/v | 1.48 ± 0.08* | 43 |
| AZONE 5% v/v, ESCALOL ® 507 3% v/v | 0.74 ± 0.02* | 2.1 |
| PARSOL ® MCX 3% v/v, ESCALOL ® 507 3% v/v | 1.30 ± 0.10* | 37 |
| Control (no enhancer) | 0.35 ± 0.10 | — | n > or = 10,
*statistically significantly different from control,
P < 0.01 following student t-test.

Table 5 shows the effect of hydroquinone (HQ) penetration across full-thickness guinea pig skin in vivo on the mean melanin content (mg/cm²)+/−standard error of the mean following the application of a finite dose solution (5 microL/cm²). Melanin content was measured by reflectance absorbance from the treated and untreated skin according to the methods outlined in the PhD thesis of Anderson, J. R., titled The Development of Techniques for Measuring the Bioavailability of Topical Depigmenting Agents (School of Pharmaceutics, Victorian College of Pharmacy Ltd., Parkville, Victoria, Australia, December, 1985).

TABLE 5

| HQ concentration/Enhancer type | Melanin content ($\mu g/cm^2$) | p value relative to control | Enhancement ratio (enhancer/ control) |
|---|---|---|---|
| HQ 1% w/v control * | 57.5 ± 3.7 | — | — |
| HQ 1% w/v, Octyl dimethyl PABA 2% v/v | 38.2 ± 3.1 | 0.002* | 1.5 |
| HQ 2% w/v control ^ | 36.8 ± 8.1 | — | — |
| HQ 2% w/v, Azone 2% v/v | 39.5 ± 9.6 | 0.35^ | 0.93 | n = 8, statistically significant differences tested for using a Student t-test.

EXAMPLE 5

Table 6 shows the median amount ($\mu g/cm^2$) of ibuprofen penetrated across full-thickness hairless mouse skin in vitro when 400 microL of a 2% w/v ibuprofen and 2% v/v dermal penetration enhancer in 70% v/v aqueous ethanol is applied. Again Azone was selected as the standard for comparison and the control formulation contained no penetration enhancer. The detection wavelength was 210 nm and the mobile phase consisted of acetonitrile:water (55:45) made to pH 3.0 with orthophosphoric acid.

TABLE 6

| Enhancer type | after 12 hours | after 24 hours |
|---|---|---|
| Octyl methoxycinnamate 2% v/v | 1099* | 2458* |
| Octyl dimethyl PABA 2% v/v | 1123* | 2981* |
| Azone 2% v/v | 1036* | 2684* |
| Control (no enhancer) | 474 | 1819 | n = 8,
*statistically significantly different from control,
p < 0.05 following ANOVA on Ranks.

EXAMPLE 6

Table 7 shows the mean amount ($\mu/cm^2$)+/−standard error of the mean of testosterone penetrated across dermatomed (300 µm thickness) neonate porcine skin in vitro when 10 microL of a 12% w/v testosterone and 8% v/v of dermal penetration enhancer in absolute ethanol was applied. The detection wavelength was 241 nm and the mobile phase consisted of acetonitrile:water (55%:45%).

TABLE 7

| Enhancer type | after 4 hours | after 24 hours |
|---|---|---|
| Octyl dimethyl PABA 8% v/v | 72 ± 10* | 227 ± 7* |
| Control (no enhancer) | 4 ± 1 | 13 ± 2* |
| Enhancement ratio | 18 | 17 | n = 3,
*statistically significantly different from control,
P < 0.003 following Student t-test.

EXAMPLE 7

Figure 4:
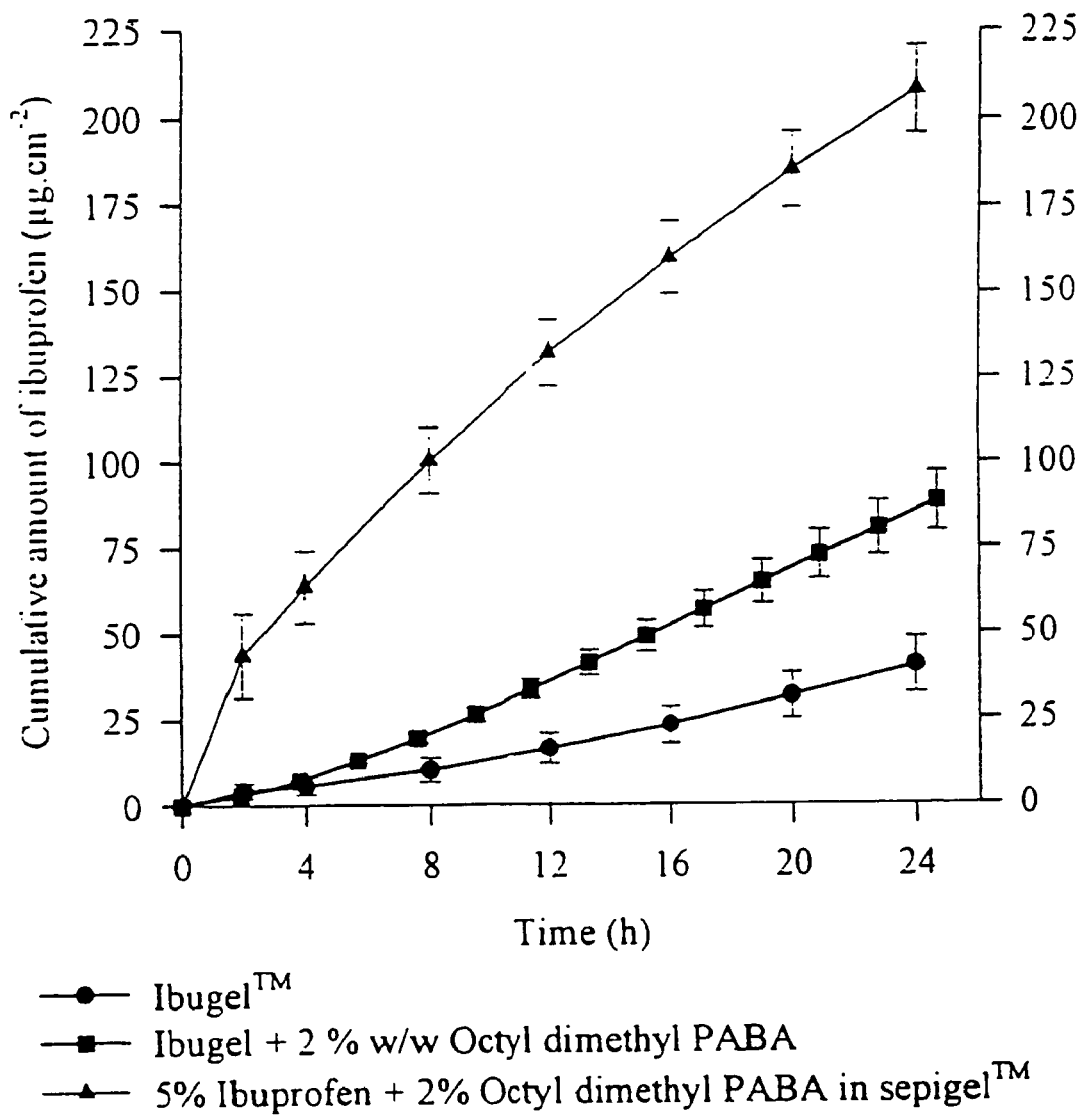
FIG. 4 is a graphical representation showing the diffusion of ibuprofen from gel formulations across shed snake skin.

FIG. 4 shows the cumulative amount of ibuprofen transferred across shed snake skin versus time for gel formulations of ibuprofen. 5 mg of each gel was applied to the skin. Samples were assayed by the HPLC method mentioned in Example 5. The gels were made to a final concentration of 5% w/w ibuprofen and 2% w/w dermal penetration enhancer by first dissolving them in 50% v/v aqueous ethanol then adding 2% w/w Sepigel-305™ (SEPPIC, Paris, France) as a gelling agent and stirring at room temperature until a gel was formed. This formulation was compared with the commercial IBUGEL™ (Dermal Laboratories, UK) formulation which contained 5% w/w ibuprofen in a ethanolic gel base formed with carbopol. As well, 2% w/w dermal penetration enhancer was added to the IBUGEL by simple mixing. The ibuprofen contents of each gel were determined by HPLC and were found to be 5.02, 5.75 and 5.43 mg/g for the gel using Sepigel-305™ and enhancer, the IBUGEL and the IBUGEL with enhancer; respectively.

Both the cumulative amounts at 12 an 24 h and the mean flux over 24 h were significantly greater (p<0.05) for both the enhanced gel formulations when compared to the commercial IBUGEL formulation. The flux enhancement ratios were 6.15 and 2.61 for the gel using Sepigel-305™ and enhancer and the IBUGEL with enhancer (n=3) respectively when compared to the IBUGEL (p<0.05).

EXAMPLE 8

Table 8 shows the mean flux ($g/cm^2.h$) of hydrocortisone penetrated across snake skin in vitro when 400 microL of 1% w/v hydrocortisone and 2% v/v octyl dimethyl PABA in 70% v/v aqueous ethanol was applied. The control formulation contained no penetration enhancer. The detection wavelength was 242 nm and the mobile phase consisted of acetonitrile: water (35%:65%).

TABLE 8

| Enhancer type | Mean flux +/− std error ($microg/cm^2 \cdot h$) | p value relative to control | Enhancement ratio |
|---|---|---|---|
| Control - no enhancer | 0.14 ± 0.04 | — | — |
| Octyl dimethyl PABA 8% v/v | 0.79 ± 0.06 | <0.0001 | 5.8 |

EXAMPLE 9

Table 9 shows the mean flux over 24 h of ketoprofen from a transdermal patch using the enhancer octyl salicylate compared with a control without enhancer. The patches were prepared by dissolving 300 mg of ketoprofen, 400 mg of penetration enhancer, 300 mg of polyethylene glycol 400 and 800 mg of hydroxypropylcellulose in 20 mL of ethanol and stirring until viscous. This was then poured onto a clean glass plate and dried at 40 degrees Celsius for 1 h. The thickness of this film was approximately 1 mm. Circles of 0.8 $cm^2$ were then cut out of this matrix and stuck onto the middle of 2.0 $cm^2$ circles of OPSITE™ adhesive bandage. This patch was then stuck onto 2.0 $cm^2$ pieces of snake skin and placed in the diffusion cell. The ketoprofen content of each patch formulation was determined by HPLC in triplicate and found to be 6.99+/−0.30 $mg/cm^2$ and 6.76+/−0.24 $mg/cm^2$, for the control and octyl salicylate patches respectively (mean content+/−std error, n=4).

TABLE 9

| Enhancer type | Mean flux +/− std error (microg/cm² · h) | p value relative to control | Enhancement ratio |
|---|---|---|---|
| Control - no enhancer | 0.47 ± 0.04 | — | — |
| Octyl salicylate | 11.70 ± 0.65 | <0.0001 | 25.2 |

In order to further illustrate the present invention and the advantages thereof, the following specific examples are given, it being understood that same are intended only as illustrative and in nowise limitative. In the examples, the effectiveness of the dermal penetration enhancers are illustrated by measuring the skin penetration of physiologically active agents. Also, the skin penetration of the dermal penetration enhancers of this invention were compared with that of other penetration enhancers as well as formulations of bio-affecting agents with common adjuvants. The comparisons made generally consisted of measuring the relative penetration through shed snake skin of the various formulations. In the examples, the in vitro skin penetration studies were performed using the same in vitro diffusion cell apparatus as previously mentioned.

EXAMPLE 10

Figure 5:
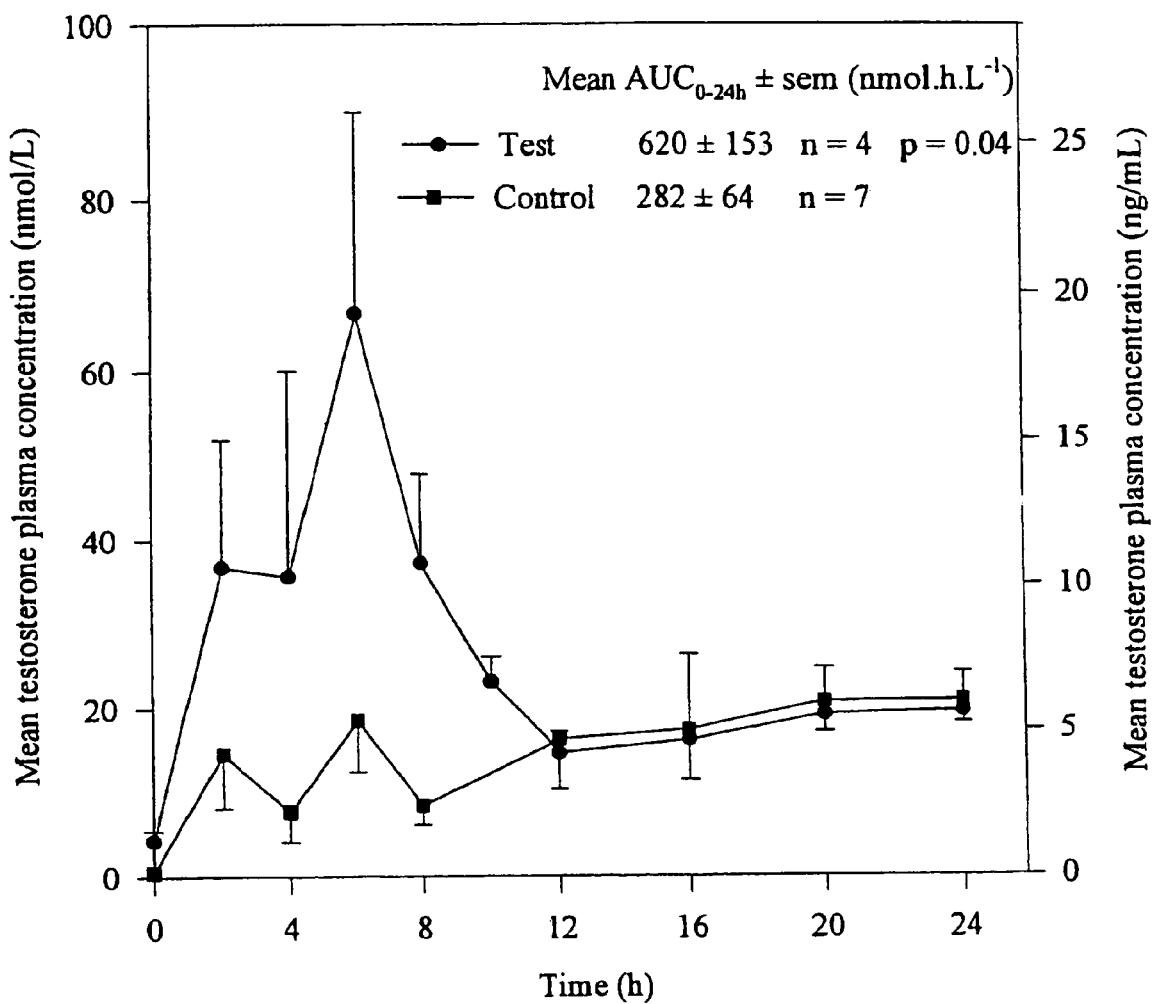
FIG. 5 is a graphical representation showing the plasma profile of testosterone in domestic weanling pigs after a single application of a metered dose topical aerosol. Error bars represent standard error of the mean.

FIG. 5 shows the mean cumulative amount of testosterone which crosses the shed snake skin versus time.

The volume of each formulation applied to the skin was 5 microL/cm². Each formulation contained 12% w/v testosterone in absolute ethanol. The dose was applied with a GC syringe. All except for the control formulation had a penetration enhancer added at a concentration of 8% v/v.

Samples were assayed for testosterone by HPLC as shown before in Example 6.

Table 10 shows the mean flux of testosterone over 24 h for each of the formulations and the degree of enhancement expressed as the ratio of the mean flux of the penetration enhancer formulation divided by the mean flux of the control formulation.

TABLE 10

| Enhancer type | Mean flux +/− std error (microg/cm² · h) | p value relative to control | Enhancement ratio |
|---|---|---|---|
| Control - no enhancer | 0.70 ± 0.03 | — | — |
| Oleic acid | 2.09 ± 0.08 | <0.0001 | 3.0 |
| Azone | 2.02 ± 0.27 | <0.03 | 2.9 |
| Octyl dimethyl PABA | 1.43 ± 0.25 | <0.03 | 2.0 |
| Octylsalicylate | 4.18 ± 0.41 | <0.03 | 6.0 |

EXAMPLE 11

Table 11 shows the mean flux over 24 h and the enhancement ratios for a number of different preferred compounds after they are applied to the skin at a dose of 5 microL/cm². The two penetration enhancers given as examples are octyl dimethyl PABA and Azone. Both penetration enhancers were again at a concentration of 8% v/v within the formulations and control was without a penetration enhancer. A concentration of 2% w/v oestradiol was used in the formulation and detection wavelength was 212 nm and the mobile phase consisted of acetonitrile:water (40%:60%). A concentration of 6% w/v progesterone was used in the formulation, the detection wavelength was 240 nm and the mobile phase consisted of acetonitrile:water (55%:45%). A concentration of 6% w/v norethisterone acetate was used in the formulation, the detection wavelength was 240 nm and the mobile phase consisted of acetonitrile:water (55%:45%) adjusted to pH 3.0 with orthophosphoric acid. A concentration of 20% ibuprofen was used in the formulation, the detection wavelength was 210 nm and the mobile phase consisted of acetonitrile:water (55%:45%) adjusted to pH 3.0 with orthophosphoric acid. A concentration of 20% flurbiprofen was used in the formulation, the detection wavelength was 247 nm and the mobile phase consisted of acetonitrile:water (55%:45%) adjusted to pH 3.0 with orthophosphoric acid.

TABLE 11

| Drug | Enhancer type | Mean flux +/− std error (microg/cm² · h) | p value cf. control | Enhancement ratio |
|---|---|---|---|---|
| Oestradiol | Control, n = 3 | 0.06 ± 0.01 | — | — |
| | Azone | 0.40 ± 0.05 | <0.003 | 6.4 |
| | Octyldimethyl PABA | 0.26 ± 0.01 | <0.0001 | 4.1 |
| Progesterone | Control, n × 3 | 0.40 ± 0.02 | — | — |
| | Azone, n = 3 | 2.17 ± 0.33 | <0.05 | 5.4 |
| | Octyl dimethyl PABA | 0.95 +/31 0.03 | <0.0001 | 2.4 |
| Norethisterone acetate | Control | 0.14 ± 0.02 | — | — |
| | Azone | 0.16 ± 0.02 | −0.0001 | 1.1 |
| | Octyl dimethyl PABA | 1.85 +/31 0.07 | <0.0001 | 12.8 |
| Ibuprofen | Control | 5.39 +/31 0.50 | — | — |
| | Azone | 13.53 ± 1.38 | 0.0014 | 2.5 |
| | Octyl dimethyl PA0BA | 13.16 ± 1.21 | 0.001 | 2.4 |
| Flurbiprofen | Control, n = 3 | 0.81 ± 0.05 | — | — |
| | Azone | 2.05 +/31 0.42 | 0.0559 | 2.5 |
| | Octyl dimethyl PABA, n = 3 | 2.91 +/31 0.30 | 0.0023 | 3.6 |

The flux values obtained for these drugs are clinically relevant, given for example that in hormone replacement therapy for postmenopausal women the current transdermal delivery systems aim to provide 25 to 100 μg of estradiol per day and 250 μg of norethisterone per day (Estracombi™) and in testosterone replacement therapies the goal ranges from replacing 0.1 to 0.3 mg per day in women lacking testosterone (U.S. Pat. No. 5,460,820), to 5 to 6 mg per day in testosterone deficient hypogonadal men (Androderm.TM.) and up to 6 to 10 mg per day for male contraception (ref. J. Clin. Endocrinol. Metab., Vol. 81, 4113-4121, 1996). For the NSAIDs, ibuprofen and flurbiprofen increased drug flux is desirably predicated on the basis that this will lead to higher local concentrations of the active drug at the target site of pain and inflammation.

EXAMPLE 12

Figure 6:
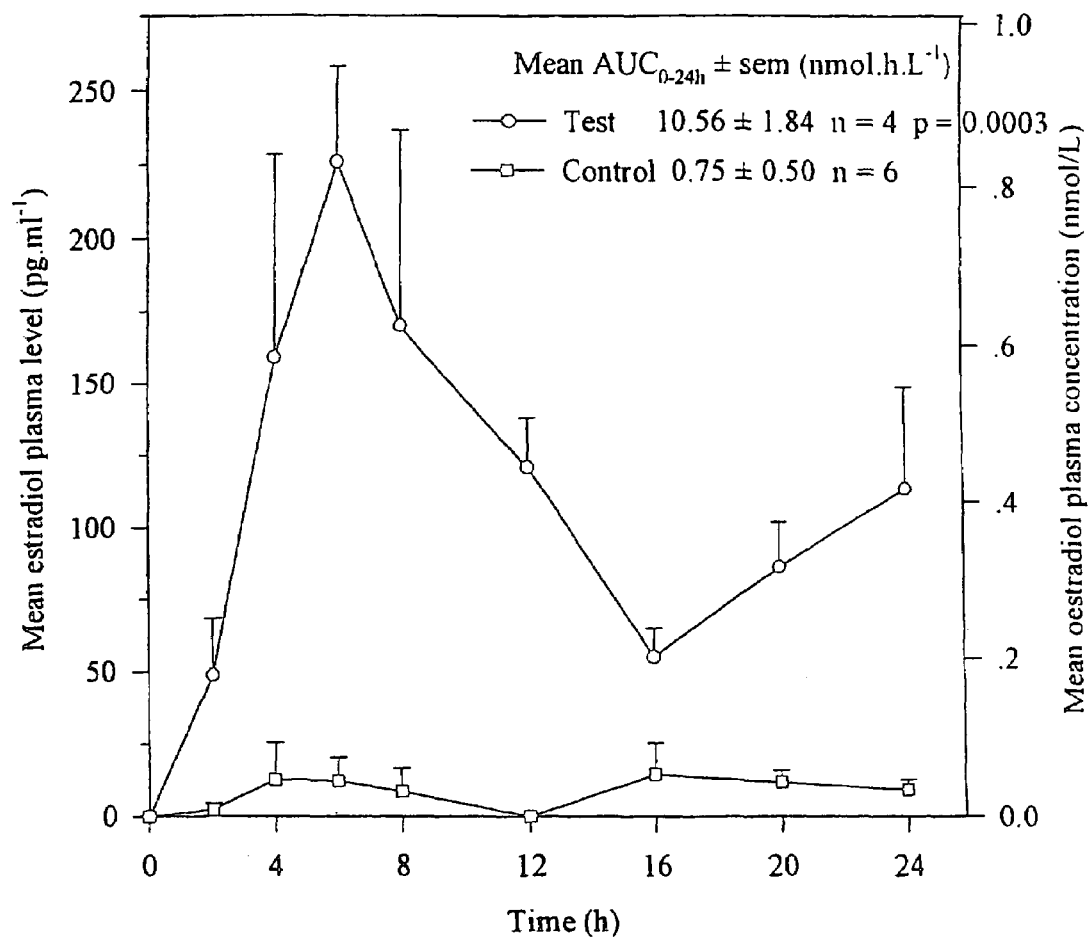
FIG. 6 is a graphical representation showing the plasma profile of estradiol in domestic weanling pigs after a single application of a metered dose topical aerosol. Error bars represent standard error of the mean.

FIGS. 5 and 6 show the mean plasma levels of testosterone and oestradiol respectively following application of the topical transdermal aerosols (described previously in examples 15 and 14 respectively) to domestic weanling pigs (7 to 8 weeks old) in vivo. Plasma testosterone and oestradiol levels were determined by high specificity radioimmunoassays, using commercially available assay kits. The oestradiol assay (Orion Diagnostica, Finland) was conducted according to the manufacturers' directions. The testosterone assay (Pantex, CAL, USA) was also conducted according to the directions, with the procedure modified to include an extraction step (90% diethylether/10% ethyl acetate) to remove any species specific matrix effects. The control formulations were the same aerosol systems as above, except they did not contain any dermal penetration enhancer.

The male pigs receiving the testosterone dose were surgically castrated 1 week prior to the commencement of the study to remove any interference from endogenous testosterone production and at the same time a cephalic cannula was inserted to facilitate blood sampling. These procedures were performed under general anaesthetic halothane (Fluothane™).

The results shown are baseline subtracted, were the baseline testosterone level at time zero was 4.3 nmol/L+/−1.1 nmol/L (mean+/−std error mean) for the test group (n=4) and was <0.5 nmol/L for every pig in the control group (n=7). A single application of 9 sprays over 180 cm$^2$ was applied at 9 am and blood samples were taken at the intervals shown over 24 h. The mean body weight of the pigs were 19.9 kg+/−0.8 kg and 17.2 kg+/−0.4 kg for the test and control groups respectively. The area under the plasma concentration versus time curve (AUC) was 2.2 fold greater (p<0.05) for the penetration enhancer formulation compared with control. The calculated results for AUC were normalised to a body weight of 20 kg assuming volume of distribution is directly proportional to body weight.

The male pigs receiving the oestradiol dose had baseline oestradiol levels of <0.02 nmol/L for every pig in the test group (n=4) and <0.02 nmol/L for every pig in the control group (n=6). A single application of 3 sprays over 30 cm$^2$ was applied at 9 am and blood samples were taken at the intervals shown over 24 h. The mean body weights of the pigs were 21.3 kg+/−1.0 kg and 17.5 kg+/−0.4 kg for the test and control group respectively. The area under the plasma versus time curve (AUC) was 14.1 fold greater (p<0.0003) for the penetration enhancer formulation compared with control. The calculated results for AUC were normalised to a body weight of 20 kg assuming volume of distribution is directly proportional to body weight.

EXAMPLE 13

Male pigs were used as described above, and the testosterone spray was applied daily over 180 cm$^2$ as described previously. Once daily testosterone application was performed at 9 am for 6 consecutive days, and on the sixth day blood samples were taken at the intervals shown over 24 h in FIG. 7. A baseline blood sample was taken at time=0 h, on day 1 and was 2.8 nmol/L+/−1.1 nmol/L (mean+/−std error mean), n=4. FIG. 7 shows the mean plasma level of testosterone versus time over 24 h. The results shown are baseline testosterone subtracted and are representative of the expected steady-state profile for testosterone.

FIG. 8 shows the mean cumulative amount of testosterone crossing the domestic weanling pig skin in vivo, as determined by Wagner-Nelson analysis, which says that Flux=Plasma conc.times.Clearance (Berner B., John V. A., Pharmacokinetic Characterisation of Transdermal Delivery Systems, Clin. Pharmacokinet., 26(2): 121-134, 1994.). Clearance was determined prior to study commencement by a bolus dose of intravenous testosterone and was found to be 663 ml/h.kg+/−139 ml/h.kg which was similar to the reported value for males of 655 ml/h.kg (Mazer N. A., Heiber W. E., Moellmer J. F., Meikle A. W., Stringham J. D., Sanders S. W., Tolman K. G., Odell W. D., Enhanced transdermal delivery of testosterone: a new physiological approach for androgen replacement in hypogonadal men, J. Control. Releas., 19, 347-362, 1992). Also included for comparison in FIG. 8 are the expected in vivo penetration across human skin and the in vitro penetration of testosterone across shed snake skin. The in vivo penetration across human skin was based on a 2.2 fold lower permeability of testosterone in human skin compared with pig skin as determined in vivo (Bartek M. J., LaBudde J., Maibach H. I., Skin Permeability In Vivo: Comparison in Rat, Rabbit, Pig and Man, J. Invest. Dermatol., 58(3): 114-123, 1972);

FIG. 8 shows the controlled nature of testosterone penetration across the skin in vivo, as well as the good predictive capability of the in vitro shed snake skin diffusion model for ascertaining the likely penetration of the testosterone across human skin. It is therefore envisaged that the flux values obtained in examples 10 and 11 will be very similar to those obtained in humans in a clinical setting.

Further to this FIG. 9 depicts the predicted plasma levels of testosterone in male subjects of a nominal weight of 70 kg based upon the clearance value of testosterone in males shown above. For comparison the 95% confidence interval of the testosterone plasma level in normal healthy adult males is given (Mazer, et al., J. Control. Releas., 19, 347-362, 1992). As shown this delivery system is quite capable of achieving the desired level of testosterone replacement in testosterone deficient hypogonadal men based upon on simple once daily application of the delivery system.

Aerosol Device

A plastic-coated glass aerosol container of 10 ml fill volume was fitted with a pharmaceutical grade metered-dose valve of a nominated discharge volume (50 µl for the oestradiol aerosol and 100 µl for the testosterone aerosol).

A stainless steel O-ring locks the valve in place on the aerosol container.

The aerosol container is charged with at least one physiologically active agent, non-volatile dermal penetration enhancer, volatile liquid carrier and optionally any other diluents, carriers, surfactants or additives followed by the propellant according to any suitable process.

A pharmaceutical grade spray nozzle and an aerosol shroud is fitted to keep the spray nozzle perpendicular to the skin at a height of 50 mm.

Method of Aerosol Use

1. Hold the device upright in the palm of your preferred hand with your thumb resting gently on the actuator button.

2. Rest the shroud opening on the skin and depress the actuator button once and release the button. Remove the device from the skin.

3. Repeat steps 1 and 2 on a new area of skin until the correct number of doses have been given.

4. Allow the applied formulation to dry on the skin for 1 minute.

During application of the spray, the nozzle shroud envelopes the spray, providing an effective closed system which deposits the active agent into the skin, and such that when the spray hits the surface of the skin it does not undergo any appreciable bounce-back into the atmosphere. A defined dose of active agent and penetration enhancer is forced through a uniform spray nozzle at a constant pressure form a defined height to give a uniform dose per $cm^2$.

EXAMPLE 14

| 17-β-Oestradiol Metered-Dose Transdermal Aerosol | |
|---|---|
| | Concentration |
| Active ingredient: | |
| 17-β-Oestradiol | 2% w/v |
| Non-volatile dermal penetration enhancer: | |
| Octyl dimethyl-para-aminobenzoate (Escalol 507, Padimate O) | 8% v/v |
| Volatile liquid: | |
| Absolute ethanol (AR) | 60% v/v |
| Volatile propellant: | |
| Dimethyl ether | 30% v/v |
| to give a final formulation pressure of 2.0 kp/cm$^2$ (30 psi). | |

One spray of 50 µl will apply 1 mg of 17-β-oestradiol over an area of approximately 10 cm.sup.2. 3 sprays will be administered to the forearm skin, applying a dose of 3 mg over approximately 30 cm$^2$.

EXAMPLE 15

| Testosterone Metered-Dose Transdermal Aerosol | |
|---|---|
| | Concentration |
| Active ingredient: | |
| Testosterone | 12% w/v |
| Non-volatile dermal penetration enhancer: | |
| Octyl dimethyl-para-aminobenzoate (Escalol 507, Padimate O) | 8% v/v |
| Volatile liquid: | |
| Absolute ethanol (AR) | 50% v/v |
| Volatile propellant: | |
| Dimethyl ether to give a final formulation pressure of 2.4 kp/cm$^2$ (35 psi). | 35% v/v |

One spray of 100 µl will apply 12 mg of testosterone over an area of approximately 20 cm$^2$. 9 sprays will be administered to a defined area of skin on the torso (rib cage), applying a dose of 108 mg over approximately 180 cm$^2$.

EXAMPLE 16

| Analgesic mousse with penetration enhancement | |
|---|---|
| Ingredient: | Concentration |
| Ibuprofen | 5% w/w |
| 2-ethylhexyl-p-methoxycinnamate | 5% w/w |
| nonionic emulsifier | 2.5% w/w |
| ethyl alcohol (95%) | 32.5% w/w |
| purified water | 50% w/w |
| hydrocarbon propellant | 5% w/w |

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

The invention claimed is:

1. An apparatus for appying a metered dose of a non-occlusive percutaneous or non-occlusive transdermal drug delivery system comprising a physiologically active agent or prodrug thereof to a dermal surface of an animal, comprising:
   (A) a container,
   (B) a metered dose applicator selected from the group consisting of a metered dose aerosol, a stored energy metered dose pump, and a manual metered dose pump, wherein said container contains
   (C) a non-occlusive percutaneous or non-occlusive transdermal drug delivery system that comprises:
      (1) a therapeutically effective amount of at least one physiologically active agent or prodrug thereof and at least one dermal penetration enhancer, which is present in an amount of from 10 to 10,000 wt % based on the weight of the active agent or prodrug thereof; and
      (2) at least one volatile liquid present in an amount to act as a vehicle for the active agent and penetration enhancer,
   wherein the dermal penetration enhancer (i) is adapted to transport the physiologically active agent across a dermal surface of an animal, when the volatile liquid evaporates, to form a reservoir or depot of a mixture comprising the penetration enhancer and the physiologically active agent within said surface and (ii) is of low toxicity to and is tolerated by the dermal surface of the animal, and
   wherein, after application of the system to an area of the dermal surface, the area becomes touch-dry within three minutes of application, and
   wherein the physiologically active agent is a hormone for contraception or hormone replacement therapy.

2. An apparatus for applying a metered dose of a non-occlusive percutaneous or non-occlusive transdermal drug delivery system comprising a physiologically active agent or prodrug thereof to a dermal surface of an animal, comprising:
   (A) a container,
   (B) a metered dose applicator selected from the group consisting of a metered dose aerosol, a stored energy metered dose pump, and a manual metered dose pump, wherein said container contains
   (C) a non-occlusive percutaneous or non-occlusive transdermal drug delivery system that comprises:
      (1) a therapeutically effective amount of at least one physiologically active agent or prodrug thereof and at least one dermal penetration enhancer, which is present in an amount of from 10 to 10,000 wt % based on the weight of the active agent or prodrug thereof and
      (2) at least one volatile liquid present in an amount to act as a vehicle for the active agent and penetration enhancer,
   wherein the dermal penetration enhancer (i) is adapted to transport the physiologically active agent across a dermal surface of an animal, when the volatile liquid evaporates, to form a reservoir or depot of a mixture comprising the penetration enhancer and the physiologically active agent within said surface and (ii) is of low toxicity to and is tolerated by the dermal surface of the animal, and
   wherein, after application of the system to an area of the dermal surface, the area becomes touch-dry within three minutes of application, and wherein the physiologically active agent comprises a progestogen other than progesterone.

3. An apparatus for applying a metered dose of a non-occlusive percutaneous or non-occlusive transdermal drug delivery system comprising a physiologically active agent or prodrug thereof to a dermal surface of an animal, comprising:
(A) a container,
(B) a metered dose applicator selected from the group consisting of a metered dose aerosol, a stored energy metered dose pump, and a manual metered dose pump, wherein said container contains
(C) a non-occlusive percutaneous or non-occlusive transdermal drug delivery system that comprises:
(1) a therapeutically effective amount of at least one physiologically active agent or prodrug thereof and at least one dermal penetration enhancer, which is present in an amount of from 10 to 10,000 wt % based on the weight of the active agent or prodrug thereof; and
(2) at least one volatile liquid present in an amount to act as a vehicle for the active agent and penetration enhancer, wherein the dermal penetration enhancer (i) is adapted to transport the physiologically active agent across a dermal surface of an animal, when the volatile liquid evaporates, to form a reservoir or depot of a mixture comprising the penetration enhancer and the physiologically active agent within said surface and (ii) is of low toxicity to and is tolerated by the dermal surface of the animal, and
wherein, after application of the system to an area of the dermal surface, the area becomes touch-dry within three minutes of application, and
wherein the physiologically active agent comprises an oestrogen and a progestogen other than progesterone.

4. An apparatus for applying a metered dose of a non-occlusive percutaneous or non-occlusive transdermal drug delivery system comprising a physiologically active agent or prodrug thereof to a dermal surface of an animal, comprising:
(A) a container,
(B) a metered dose applicator selected from the group consisting of a metered dose aerosol, a stored energy metered dose pump, and a manual metered dose pump, wherein said container contains
(C) a non-occlusive percutaneous or non-occlusive transdermal drug delivery system that comprises:
(1) a therapeutically effective amount of at least one physiologically active agent or prodrug thereof and at least one dermal penetration enhancer, which is present in an amount of from 10 to 10,000 wt % based on the weight of the active agent or prodrug thereof; and
(2) at least one volatile liquid present in an amount to act as a vehicle for the active agent and penetration enhancer, wherein the dermal penetration enhancer (i) is adapted to transport the physiologically active agent across a dermal surface of an animal, when the volatile liquid evaporates, to form a reservoir or depot of a mixture comprising the penetration enhancer and the physiologically active agent within said surface and (ii) is of low toxicity to and is tolerated by the dermal surface of the animal, and
wherein, after application of the system to an area of the dermal surface, the area becomes touch-dry within three minutes of application, and
wherein the active agent comprises at least one active agent selected from the group consisting of oestradiol, oestriol, oestrone, ethinyloestradiol, mestranol, stilboestrol, dienoestrol, epioestriol, estropipate, zeranol, progesterone, allyloestrenol, dydrogesterone, lynoestrenol, norgestrel, norethyndrel, norethisterone, norethisterone acetate, gestodene, levenorgestrel, medroxyprogesterone and megestrol.

5. An apparatus for applying a metered dose of a non-occlusive percutaneous or non-occlusive transdermal drug delivery system comprising a physiologically active agent or prodrug thereof to a dermal surface of an animal, comprising:
(A) a container,
(B) a metered dose applicator selected from a metered dose aerosol, a stored energy metered dose pump and a manual metered dose pump, wherein said container contains
(C) a non-occlusive percutaneous or non-occlusive transdermal drug delivery system that comprises:
(1) a therapeutically effective amount of at least one physiologically active agent or prodrug thereof and at least one dermal penetration enhancer, which is present in an amount of from 10 to 10,000 wt % based on the weight of the active agent or prodrug thereof; and
(2) at least one volatile liquid present in an amount to act as a vehicle for the active agent and penetration enhancer, wherein the physiologically active agent comprises an oestrogen, and
wherein the dermal penetration enhancer (i) is adapted to transport the physiologically active agent across a dermal surface of an animal, when the volatile liquid evaporates, to form a reservoir or depot of a mixture comprising the penetration enhancer and the physiologically active agent within said surface and (ii) is of low toxicity to and is tolerated by the dermal surface of the animal, and wherein, after application of a metered dose of the system to an area of the dermal surface, the area becomes touch-dry within three minutes of application.

* * * * *